US012053249B2

(12) United States Patent
Suga et al.

(10) Patent No.: US 12,053,249 B2
(45) Date of Patent: Aug. 6, 2024

(54) INTERFACE AND SURGERY ASSIST ROBOT

(71) Applicants: MEDICAROID CORPORATION, Kobe (JP); KAWASAKI JUKOGYO KABUSHIKI KAISHA, Kobe (JP)

(72) Inventors: Kazunori Suga, Kobe (JP); Yasuhiko Hashimoto, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 547 days.

(21) Appl. No.: 17/227,414

(22) Filed: Apr. 12, 2021

(65) Prior Publication Data

US 2021/0322111 A1 Oct. 21, 2021

(30) Foreign Application Priority Data

Apr. 15, 2020 (JP) ................................ 2020-072869

(51) Int. Cl.
*A61B 34/30* (2016.01)
*A61B 34/00* (2016.01)
*A61B 46/10* (2016.01)

(52) U.S. Cl.
CPC .............. *A61B 34/25* (2016.02); *A61B 34/70* (2016.02); *A61B 46/10* (2016.02)

(58) Field of Classification Search
CPC . A61B 19/201; A61B 19/203; A61B 19/5244; A61B 34/00; A61B 34/30; A61B 34/25; A61B 34/70
See application file for complete search history.

(56) References Cited

U.S. PATENT DOCUMENTS

| 8,672,922 B2 | 3/2014 | Loh et al. |
| 10,258,419 B2 | 4/2019 | Auld et al. |
| 2011/0015483 A1 | 1/2011 | Barbagli et al. |
| 2012/0211546 A1 | 8/2012 | Shelton, IV |
| 2014/0148819 A1 | 5/2014 | Inoue et al. |

(Continued)

FOREIGN PATENT DOCUMENTS

| CN | 107771065 A | 3/2018 |
| EP | 2623049 A1 | 8/2013 |

(Continued)

OTHER PUBLICATIONS

Yasuhisa Hasegawa et al: "Smart arm—User interface", Systems, control and information, 2019, vol. 63, No. 10, pp. 424-430, The Institute of Systems, Control and Information Engineers, Japan.

*Primary Examiner* — Vi X Nguyen
(74) *Attorney, Agent, or Firm* — METROLEX IP LAW GROUP, PLLC

(57) ABSTRACT

An interface according to an embodiment may be arranged between a driver provided to a robotic arm and a manual surgical instrument. The interface includes: a driven unit to be connected to the driver and be driven by a driving force transmitted from the driver provided to the robotic arm; a manipulation portion to be driven by a driving force transmitted by the driven unit to manipulate an operation-target portion of the manual surgical instrument; and a surgical instrument holder configured to hold the manual surgical instrument in a state where the operation-target portion of the manual surgical instrument is positioned with respect to the manipulation portion.

20 Claims, 16 Drawing Sheets

(56) References Cited

U.S. PATENT DOCUMENTS

2014/0222023 A1\* 8/2014 Kim ................ A61B 34/30
606/130
2018/0126504 A1\* 5/2018 Shelton, IV ......... A61B 17/068

FOREIGN PATENT DOCUMENTS

| EP | 3613377 A1 | 2/2020 |
| JP | 2013-034832 A | 2/2013 |
| WO | 2017/071447 A1 | 5/2017 |
| WO | 2017/089908 A1 | 6/2017 |

\* cited by examiner

INTERFACE AND SURGERY ASSIST ROBOT

CROSS REFERENCE TO RELATED APPLICATIONS

This application claims priority to Japanese Patent Application No. 2020-072869 filed on Apr. 15, 2020, the entire contents of which are incorporated herein by reference.

BACKGROUND

The disclosure may relate to an interface and a surgery assist robot.

In a related art, there is known a surgery assist robot to which a surgical tool is attached.

U.S. Patent Application Publication No. 2012/0211546 discloses a surgery assist robot including a plurality of robotic manipulators. Each of the plurality of robotic manipulators is configured as an articulated robot. To the plurality of robotic manipulators, surgical tools are respectively attached.

In the surgery assist robot, each of the surgical tools includes a tool attachment portion that attaches the surgical tool to the robot manipulator. The tool attachment portion is provided with rotation members. The rotation members of the tool attachment portion are driven to rotate by drivers provided in the robot manipulator. By the rotational forces of the rotation members, the surgical tool (e.g., end cutter) or the like is driven. Although not specified in the above Patent Application Publication, generally, the surgical tool attached to the robot manipulator is manufactured as a dedicated product compatible with (dedicated for) the mechanism (e.g., the drivers) of the robot manipulator.

SUMMARY

However, in the surgery assist robot as described above, the surgical tool to be attached to the robot manipulator is manufactured as the dedicated product so as to compatible with (dedicated for) the mechanism or the like of the robot manipulator. Therefore, there may be a problem that existing surgical instruments, owned by the hospital or the like and manually operated by doctors or the like, can not be operated by such a robot manipulator.

An object of an embodiment of the disclosure may be to provide an interface and a surgery assist robot that can operate an existing manual surgical instrument without using a surgical instrument dedicated for the surgery assist robot.

A first aspect of the disclosure may be an interface for connecting a manual surgical instrument to a driver provided to a robotic arm in such a manner that the manual surgical instrument is operable by a driving force transmitted from the driver. The interface includes: a driven unit to be connected to the driver and be driven by the driving force transmitted from the driver; a manipulation portion to be driven by the driven unit and manipulate an operation-target portion of the manual surgical instrument; and a surgical instrument holder configured to hold the manual surgical instrument at a position where the operation-target portion of the manual surgical instrument is positioned with respect to the manipulation portion.

As described above, the interface according to the first aspect includes: the driven unit to be connected to the driver and be driven by the driving force transmitted from the driver; and the manipulation portion to be driven by the driven unit to manipulate the operation-target portion of the manual surgical instrument. Therefore, the operation-target portion of the manual surgical instrument can be operated by the manipulation portion of the interface being driven (moved) by the driving force of the driver provided to the robotic arm. As a result, the existing manual surgical instrument can be operated without using a surgical instrument dedicated for the robotic arm. Further, the interface according to the first embodiment includes the surgical instrument holder configured to hold the manual surgical instrument at the position where the operation-target portion of the manual surgical instrument is positioned with respect to the manipulation portion. Accordingly, since the operation-target portion of the manual surgical instrument is positioned with respect to the manipulation portion, the manual surgical instrument can be easily attached to the surgical instrument holder.

A second aspect of the disclosure may be an interface for connecting a manual surgical stapler to a driver provided to a robotic arm in such a manner that the surgical stapler is operable by a driving force transmitted from the driver. The interface may include: a driven unit to be connected to the driver and be driven by the driving force transmitted from the driver; a manipulation portion to be driven by the driven unit and manipulate an operation-target portion of the surgical stapler; and a surgical instrument holder configured to hold the surgical stapler at a position where the operation-target portion of the surgical stapler is positioned with respect to the manipulation portion.

A third aspect of the disclosure may be a surgery assist robot including a robotic arm including a driver for driving a robotic surgical instrument and an interface provided between the driver and a manual surgical instrument. The interface includes: a driven unit to be connected to the driver and be driven by the driving force transmitted from the driver provided to the robotic arm; a manipulation portion to be driven by the driving force transmitted by the driven unit to manipulate an operation-target portion of the manual surgical instrument; and a surgical instrument holder configured to hold the manual surgical instrument at a position where the operation-target portion of the manual surgical instrument is positioned with respect to the manipulation portion.

As described above, the surgery assist robot according to the third aspect includes the interface that includes: the driven unit to be connected to the driver and be driven by the driving force transmitted from the driver; and the manipulation portion to be driven by the driven unit to manipulate the operation-target portion of the manual surgical instrument. Therefore, the operation-target portion of the manual surgical instrument can be operated by the manipulation portion of the interface being driven (moved) by the driving force of the driver provided to the robotic arm. As a result, it is possible to provide the surgery assist robot that can operate an existing manual surgical instrument without using the dedicated robotic surgical instrument. Further, the interface according to the third aspect includes the surgical instrument holder configured to hold the manual surgical instrument at the position where the operation-target portion of the manual surgical instrument is positioned with respect to the manipulation portion. Accordingly, since the operation-target portion of the manual surgical instrument is positioned with respect to the manipulation portion, the manual surgical instrument can be easily attached to the surgical instrument holder.

DETAILED DESCRIPTION

Figure 1:
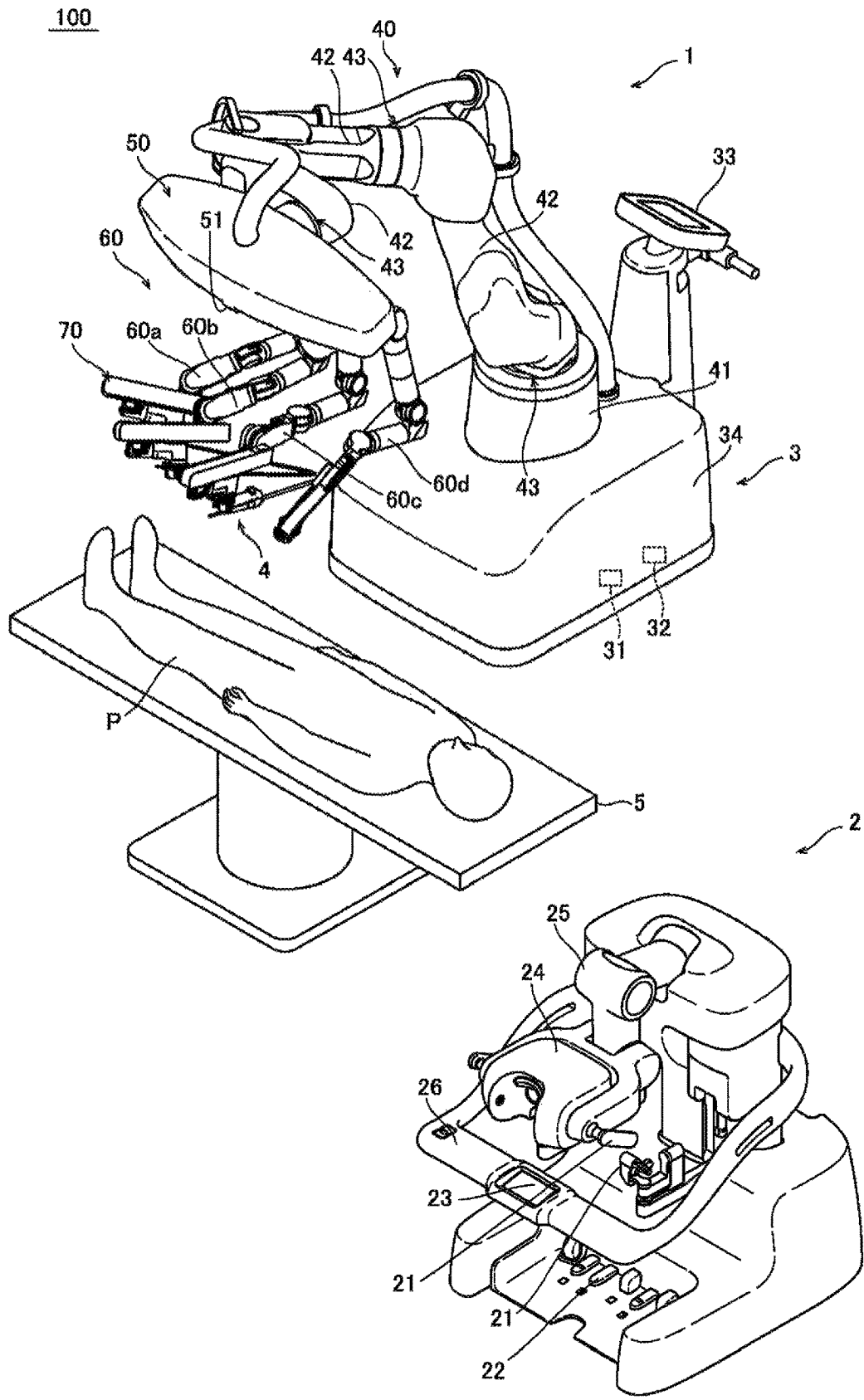
FIG. 1 is a diagram illustrating a view of a configuration of a surgical operation system according to a first embodiment.

Descriptions are provided hereinbelow for one or more embodiments of the disclosure based on the drawings. In the respective drawings referenced herein, the same constituents are designated by the same reference numerals and duplicate explanation concerning the same constituents is omitted. All of the drawings are provided to illustrate the respective examples only.

First Embodiment

A configuration of a surgical operation system 100 according to a first embodiment is described with reference to FIGS. 1 to 15.

First, a case where medical instruments 4 dedicated for a medical manipulator 1 are attached to the medical manipulator 1 is described below.

Figure 2:
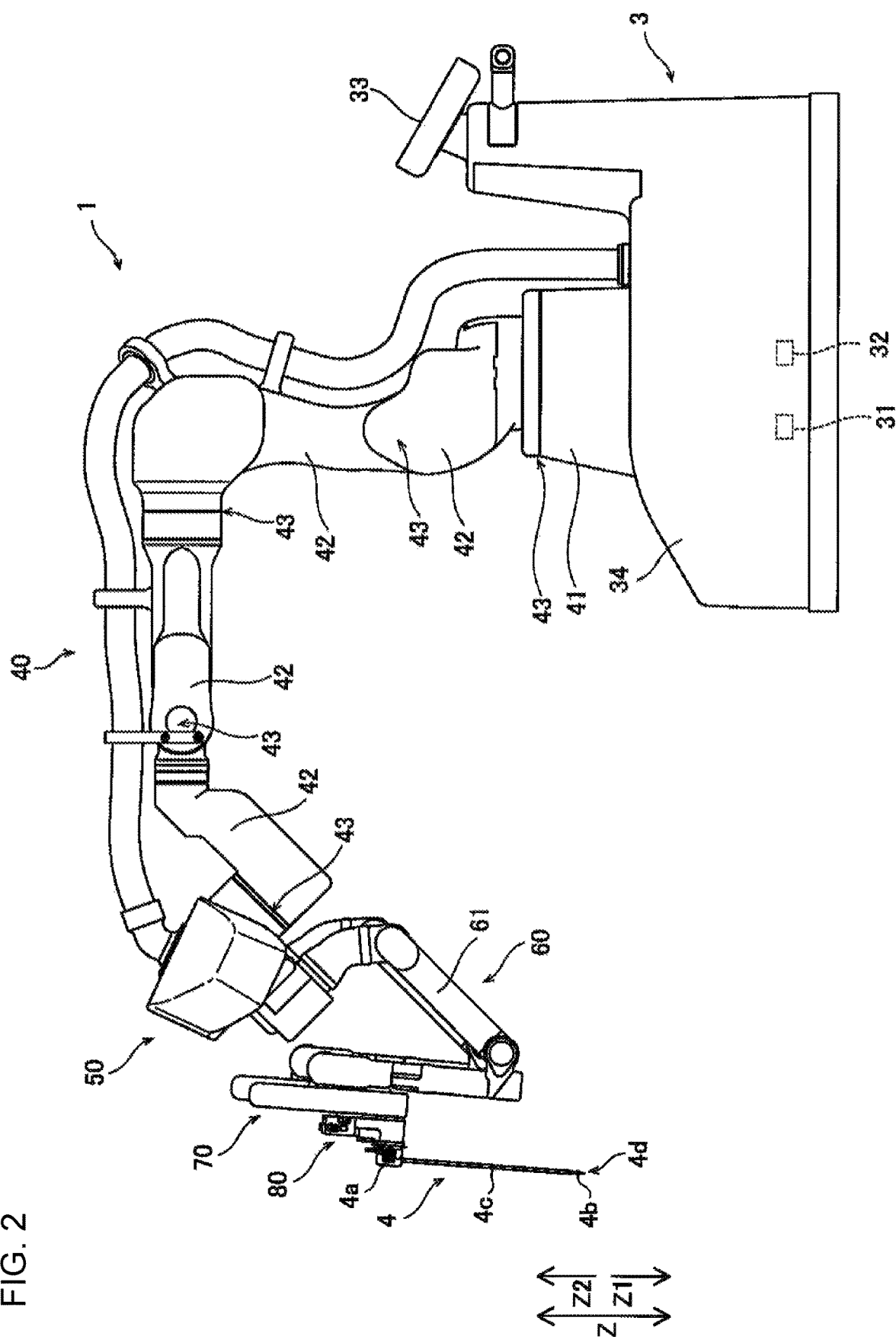
FIG. 2 is a diagram illustrating a view of a configuration of a medical manipulator according to a first embodiment.
Figure 3:
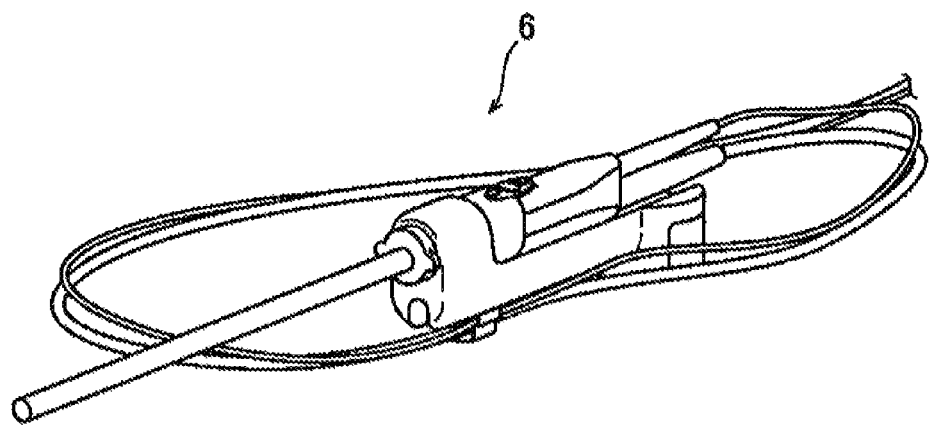
FIG. 3 is a diagram illustrating a view of an endoscope.

As illustrated in FIGS. 1 and 2, the surgical operation system 100 includes the medical manipulator 1 serving as a patient-side apparatus and a remote control apparatus 2 serving as an operator-side apparatus to operate the medical manipulator 1. The medical manipulator 1 is provided with a medical trolley 3 and is thus configured to be movable. The remote control apparatus 2 is provided at a location away from the medical manipulator 1. The medical manipulator 1 is configured to be remotely operated by the remote control apparatus 2. An operator or a surgeon inputs, to the remote control apparatus 2, an instruction that causes the medical manipulator to perform a desired operation. The remote control apparatus 2 transmits the input instruction to the medical manipulator 1. The medical manipulator 1 operates in response to the received instruction. The medical manipulator 1 is disposed in a surgery room, as a sterile field, which is sterilized. The medical manipulator 1 is an example of a surgery assist robot.

The remote control apparatus 2 is disposed inside the surgery room or outside the surgery room, for example. The remote control apparatus 2 includes operation manipulator arms 21, operation pedals 22, a touch panel 23, a monitor 24, a support arm 25, and a support bar 26. The operation manipulator arms 21 constitute operation handles for the operator to input instructions. The monitor 24 is a display (a display device) of a scope type configured to display an image captured by an endoscope 6. The support arm 25 supports the monitor 24 in such a manner that the height of the monitor 24 can be adjusted to the operator's face level. The touch panel 23 is disposed on the support bar 26. When a sensor(s) provided in the vicinity of the monitor 24 detects the head of the operator, the medical manipulator 1 can be operated by the remote control apparatus 2. The operator operates the operation manipulator arms 21 and the operation pedals 22, while viewing the surgical site displayed on the monitor 24. With this, the instruction is inputted to the remote control apparatus 2. The instruction that is inputted to the remote control apparatus 2 is transmitted to the medical manipulator 1.

The medical trolley 3 is provided with a control unit 31 that controls movement of the medical manipulator 1 and a storage 32 that stores therein programs for controlling the movement of the medical manipulator 1. Based on the instruction inputted to the remote control apparatus 2, the control unit 31 of the medical trolley 3 controls the movement of the medical manipulator 1.

Further, the medical trolley 3 is provided with an input device 33. The input device 33 is configured to accept operations to move or change posture of a positioner 40, an arm base 50, and arms 60, mainly to prepare for surgery in advance.

As illustrated in FIGS. 1 and 2, the medical manipulator 1 is disposed in the surgery room. The medical manipulator 1 includes the medical trolley 3, the positioner 40, the arm base 50, and the arms 60. The arm base 50 is attached to the distal end of the positioner 40. The arm base 50 is in a relatively long rod shape (elongate shape). Base portions (proximal end portions) of the arms 60 are attached to the arm base 50. Each of the arms 60 is configured to be foldable into a folded posture (a storage posture). The arm base 50 and the arms 60 are used being covered with a sterile drape (not illustrated).

The positioner 40 is configured as a 7-axis articulated robot. The positioner 40 is disposed on a casing 34 of the medical trolley 3. The positioner 40 is configured to move the arm base 50. Specifically, the positioner 40 is configured to three-dimensionally move the position of the arm base 50.

The positioner 40 includes a base portion 41 and link portions 42 connected to the base portion 41. The link portions 42 are connected to each other via joints 43.

As illustrated in FIG. 1, to the distal end of each of the robot arms 60, the medical instrument 4 is attached. The medical instrument 4 may be, for example, a surgical instrument (see FIG. 2), an endoscope 6 (see FIG. 3), or the like that are replaceable.

As illustrated in FIG. 2, the surgical instrument as the medical instrument 4 is provided with a drive unit 4a, which is driven by servo-motors M2 provided in a holder 71 of the arm 60. At the distal end of the surgical instrument, an end effector 4b is provided. An example of the end effector 4b that has one or more joints may be a pair of forceps, a pair of scissors, a grasper, a needle holder, a micro dissector, a staple applier, a tacker, a suction and irrigation tool, a snare wire, a clip applier, or the like. An example of the end effector 4b that has no joints may be a cutting blade, an ablation probe, an irrigation device, a catheter, a suction orifice, or the like. The medical instrument 4 includes a shaft 4c that connects the drive unit 4a and the end effector 4b. The drive unit 4a, the shaft 4c, and the end effector 4b are arranged along the Z direction.

Next, the configuration of the arm 60 is described in detail.

Figure 4:
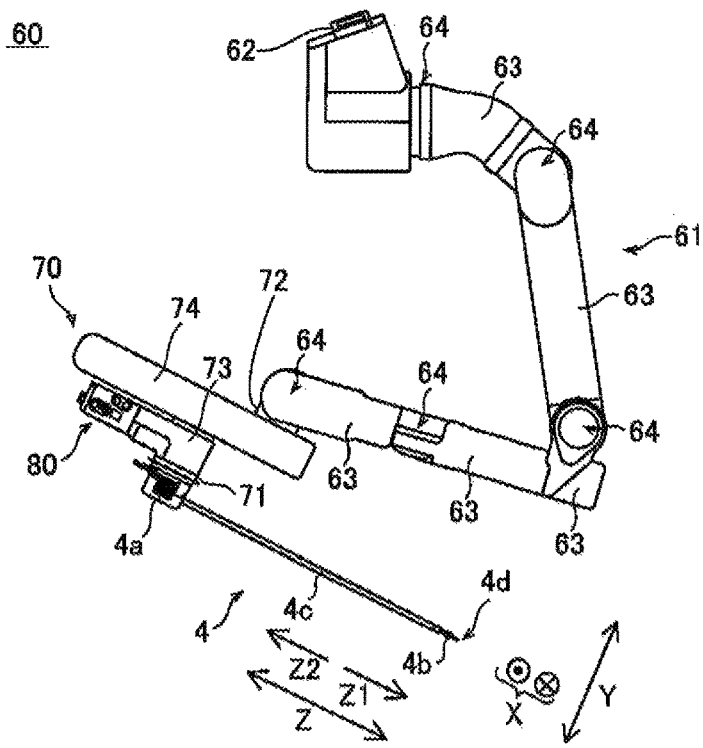
FIG. 4 is a diagram illustrating a view of a configuration of an arm of the medical manipulator according to a first embodiment.

As illustrated in FIG. 4, the arm 60 includes an arm section 61 (the base portion 62, the link portions 63, the joints 64) and a translation movement mechanism 70 provided at the distal end portion of the arm section 61. The arm 60 is configured such that the distal end side of the arm 60 is three-dimensionally movable with respect to the proximal end side (the arm base 50) of the arm 60. The plurality of the arms 60 have the same configuration.

The translation movement mechanism 70 is provided on a side of the distal end of the arm section 61. The medical instrument 4 is attached to the translation movement mechanism 70. The translation movement mechanism 70 translationally moves the medical instrument 4 in the insertion direction of the medical instrument 4 into a patient P. The translation movement mechanism 70 is configured to translationally move the medical instrument 4 relative to the arm section 61. Specifically, the translation movement mechanism 70 is provided with the holder 71 configured to hold the medical instrument 4. The holder 71 accommodates therein the servo motors M2 (see FIG. 15). The servo motors M2 are configured to rotate rotors (rotation members) provided in the drive unit 4a of the medical instrument 4. The end effector 4b is operated when the rotors (the rotation members) in the drive unit 4a are rotated. Note that when a manual surgical instrument 200 (see FIG. 6) is attached to the arm 60 instead of the dedicated medical instrument 4, the servo motors M2 drive a driven unit 320 of a later-described interface 300 (or interface device 300).

The arm 60 is configured to be attachable to and detachable from the arm base 50.

The arm section 61 is configured as a 7-axis articulated robot arm. The arm section 61 includes the base portion 62 that connects the arm section 61 to the arm base 50 and the plural link portions 63 connected to the base portion 62. The plural link portions 63 are connected to each other via the joints 64.

The translation movement mechanism 70 is configured to translationally move the holder 71 along the Z direction so as to translationally move the medical instrument 4 attached to the holder 71 along the Z direction (the extending direction or the longitudinal direction of the shaft 4c). Specifically, the translation movement mechanism 70 includes a proximal side link unit 72 connected the distal end of the arm section 61, a distal side link unit 73, and a connecting link unit 74 provided between the proximal side link unit 72 and the distal side link unit 73. The holder 71 is provided at the distal side link unit 73.

The connecting link unit 74 of the translation movement mechanism 70 functions as a double speed mechanism that makes a movement speed of the distal side link unit 73 with respect to the proximal side link unit 72 along the Z direction twice as a movement speed of the proximal side link unit 72 with respect to the connecting link unit 74 along the Z direction. The translation movement mechanism 70 is configured to translationally move the medical instrument 4 attached to the holder 71 along the Z direction by moving the distal side link unit 73 with respect to the proximal side link unit 72 along the Z direction. The proximal side link unit 72 is connected to the distal end of the arm section 61 in such a manner that the proximal side link unit 72 is rotatable about a rotational axis extending the Y direction orthogonal to the Z direction.

As illustrated in FIG. 1, the endoscope 6 is attached to one of the plural arms 60 (for example, the arm 60b), and the medical instruments 4 other than the endoscope 6 are attached to the other arms 60 (for example, the arms 60a, 60c, and 60d).

Figure 5:
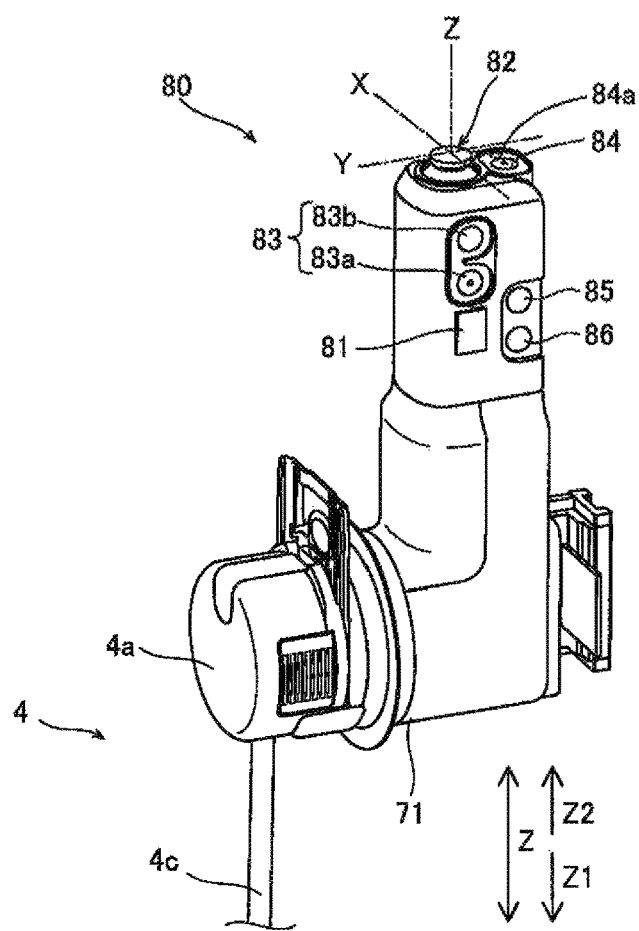
FIG. 5 is a diagram illustrating a perspective view of a configuration of an arm operation unit of the medical manipulator according to a first embodiment.

As illustrated in FIG. 5, the medical manipulator 1 includes an arm operation unit 80 that is attached to each of the arms 60 to operate the arm 60. The arm operation unit 80 includes an enable switch 81, a joystick 82, and a switch section 83. The enable switch 81 enables or disables movement of the arm 60 according to the joystick 82 and the switch section 83. When the enable switch 81 being depressed by an operator (nurse, assistant, etc.) gripping the arm operation unit 80, movement of the medical instrument 4 by the arm 60 is allowed.

Specifically, the enable switch 81 is configured as a push button switch that is to be pressed by an operator's finger or thumb. The joystick 82 is configured to be operated by being tilted by the operator (operator's finger or thumb). According to the direction of the joystick 82 being tilted and the angle of the tilt of the joystick 82, the arm 60 is controlled to move.

The joystick 82 is configured to operate the movement of the medical instrument 4 by the arm 60 in such a manner that the distal end 4d (see FIG. 4) of the medical instrument 4 moves on a predetermined plane. The switch section 83 operates the arm 60 to move the medical instrument 4 in such a manner that the distal end 4d of the medical instrument 4 moves along the longitudinal direction of the medical instrument 4 orthogonal to the predetermined plane. The switch section 83 includes: a switch 83a for moving the distal end 4d of the medical instrument 4 in the direction in which the medical instrument 4 is inserted into the patient P along the longitudinal direction of the medical instrument 4; and a switch 83b for moving the distal end 4d of the medical instrument 4 in the direction opposite to the direction in which the medical instrument 4 is inserted into the patient P.

The arm operation unit 80 includes a pivot button 85 for setting a pivot position PP that serves as a fulcrum for the movement of the medical instrument 4 attached to the arm 60. The arm operation unit 80 is provided with an adjustment button 86 for optimizing the position of the arm 60.

The arm operation unit 80 includes a mode switching button 84 for switching between a mode for eccentric movement of the medical instrument 4 attached to the arm 60 and a mode for rotational movement of the medical instrument 4 attached to the arm 60. In the vicinity of the mode switching button 84, a mode indicator 84a is provided. The mode indicator 84a displays the switched mode (the current mode).

As illustrated in FIG. 4, the arm operation unit 80 is provided to the translation movement mechanism 70. The arm operation unit 80 is attached to the translation movement mechanism 70 in such a manner that the arm operation unit 80 is arranged side by side with the medical instrument 4 attached to the translation movement mechanism 70.

(Configurations of Medical Instrument, Adaptor, Drape, and Arm)

Figure 6:
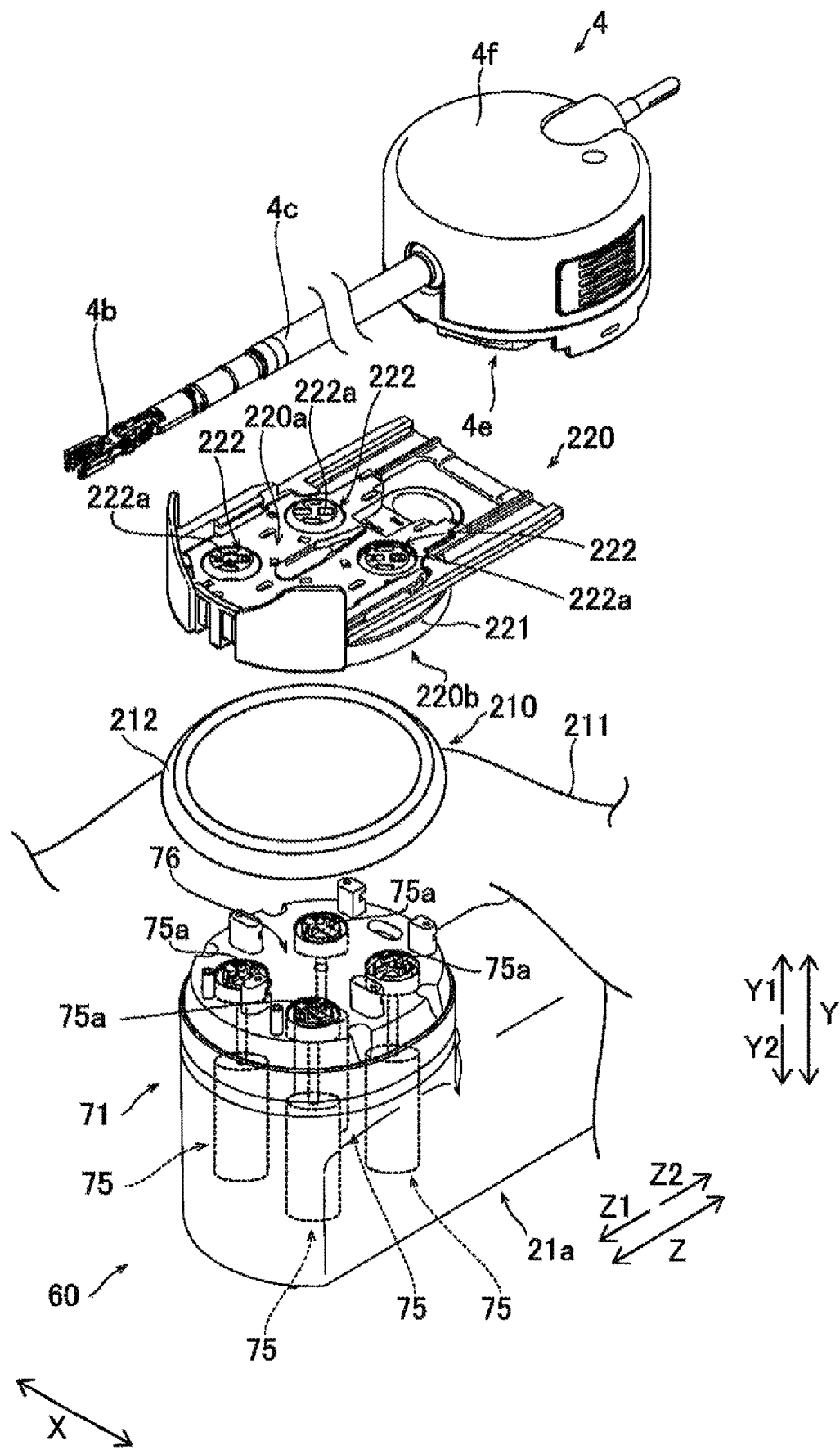
FIG. 6 is a diagram illustrating a perspective view of a state where an adaptor and a medical instrument (a dedicated robotic surgical instrument) are detached from drivers of the arm according to a first embodiment.

With reference to FIG. 6, the configurations of the medical instrument 4, an adaptor 220, a drape 210, and the arm 60 are described.

As illustrated in FIG. 6, the medical instrument 4 is detachably connected to the arm 60 through the adaptor 220. The adaptor 220 is arranged between the holder 71 (drivers 75) of the arm 60 and the medical instrument 4. The adaptor 220 is a drape adaptor for holding the drape 210 and is to be replaced by the user after each surgery. Accordingly, the drape 210 can be held by using the adaptor 220. The drape 210 is for covering the arm 60 and is sterilized. The adaptor 220 is configured to put the drape 210 between the adaptor 220 and the arm 60.

The medical instrument 4 includes a connection portion 4e, serving as an attachment surface, provided on the Y2 side of the medical instrument 4, and the connection portion 4e of the medical instrument 4 is to be attached to and connected to the adaptor 220. The connection portion 4e is provided at a housing 4f and is attached to the arm 60 via the adaptor 220. The adaptor 220 includes a connection portion 220a, serving as an attachment surface, provided on the Y1 side of the adaptor 220, and the medical instrument 4 is to be attached to and connected to the connection portion 220a of the adaptor 220. The adaptor 220 includes a connection portion 220b, serving as an attachment surface, provided on the Y2 side of the adaptor 220, and the connection portion 220b of the adaptor 220 is to be attached and connected to the holder 71 (the drivers 75) of the arm 60. The holder 71 (the drivers 75) of the arm 60 includes a connection portion 76, serving an attachment surface, provided on the Z1 side of the arm 60, and the adaptor 220 is to be attached and connected to the connection portion 76 of the arm 60.

The arm 60 is used in a clean area and is thus covered with the drape 210, as illustrated in FIG. 6. In operation rooms, clean technique is used in order to prevent surgical incision sites and the medical instruments or medical devices from being contaminated by pathogen, foreign matters, or the like. The clean technique defines a clean area and a contaminated area, which is outside the clean area. The surgery sites are located in the clean area. Members of the surgical team including the operator make sure that only sterile objects are placed in the clean area during surgery and perform sterilization for an object which is to be moved to the clean area from the contaminated area. Similarly, when the members of the surgical team including the operator place their hands in the contaminated area, the members sterilize their hands before directly touching objects located in the clean area. Instruments to be used in the clean area are sterilized or are covered with the drapes 210 sterilized.

The drape 210 includes a body section 211 that covers the arm 60 and an attachment section 212 that is sandwiched between the holder 71 (the drivers 75) of the arm 60 and adaptor 220. The body section 211 is configured as a flexible film member. The flexible film member is made of a resin material, such as thermoplastic polyurethane and polyethylene. The body section 211 includes an opening so that the drivers 75 (driving parts 75) of the arm 60 are engageable with the adaptor 220. To the opening of the body section 211, the attachment section 212 is provided so as to close the opening. The attachment section 212 is configured as a resin mold member. The resin mold member is made of a resin material such as polyethylene terephthalate. The attachment section 212 is harder (less flexible) than the body section 211. The attachment section 212 includes an opening so that the drivers 75 of the arm 60 are engageable with the adaptor 220. The opening of the attachment section 212 may be provided corresponding to the section where the drivers 75 of the arm 60 are engaged with the adaptor 220. The opening of the attachment section 212 may include plural openings corresponding to plural sections at which the drivers 75 of the arm 60 are engaged with the adaptor 220.

Figure 7:
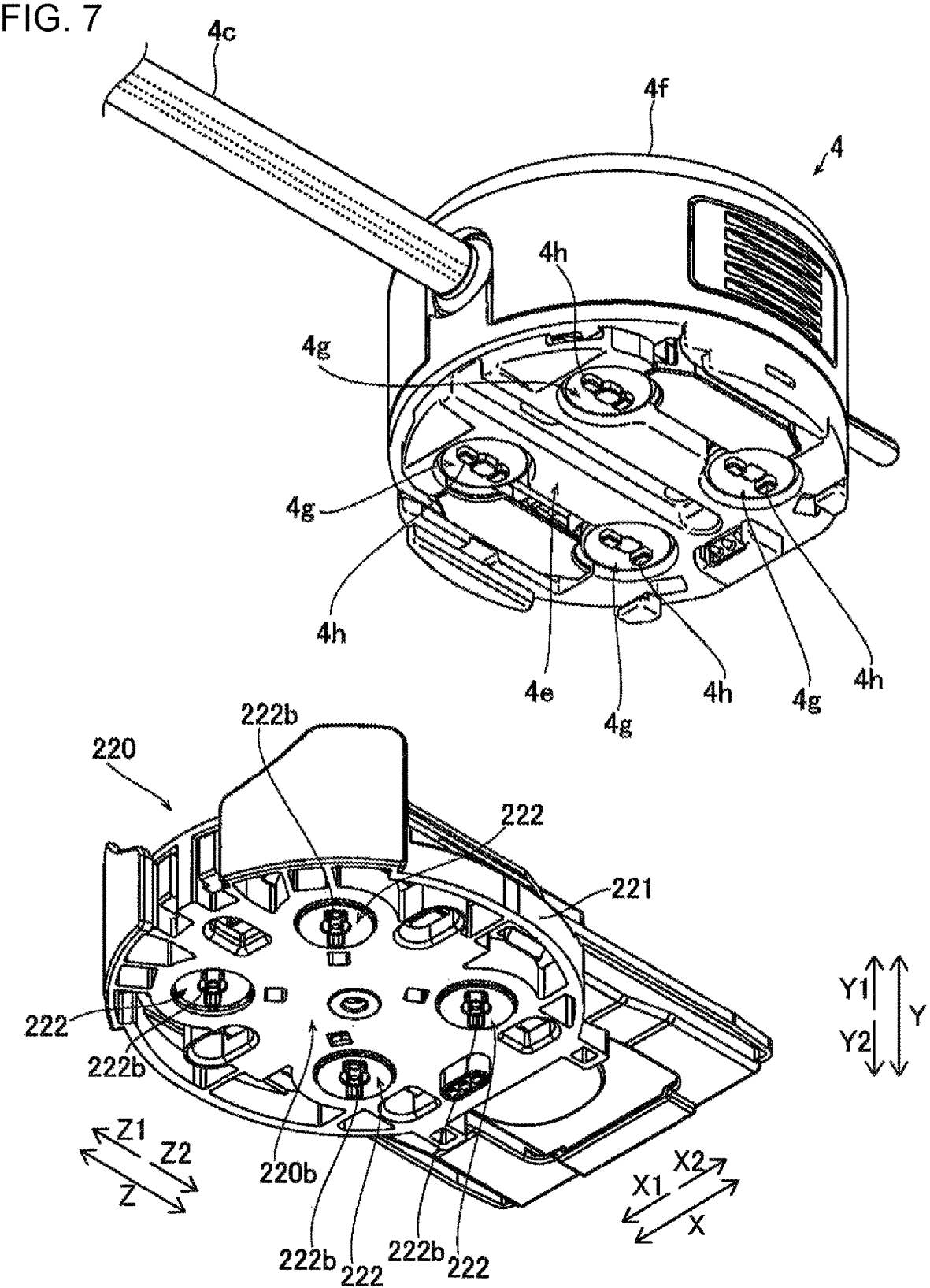
FIG. 7 is a diagram illustrating a perspective view of the adaptor and the dedicated robotic surgical instrument as seen from the Y2 side according to a first embodiment.

As illustrated in FIGS. 6 and 7, the adaptor 220 includes an adaptor main body 221 and plural (four) drive transmission members 222 supported by the adaptor main body 221 to be rotatable about respective rotational axes extending in the Y direction with respect to the adaptor main body 221. The plural drive transmission members 222 are provided in the adaptor main body 221 to be rotatable about their rotation axes. The number (four) of the plural drive transmission members 222 provided corresponds to the number (four) of plural driven members 4g of the medical instrument 4. The drive transmission members 222 are configured to transmit driving forces from the arm 60 to the driven members 4g of the medical instrument 4. Each of the drive transmission members 222 includes a fitting recess 222a, which is to be fitted with a fitting protrusion 4h of a corresponding one of the driven members 4g of the medical instrument 4. The fitting recess 222a is provided at a surface of the drive transmission member 222 on the Y1 side (the medical instrument 4 side) and is recessed from the Y1-side surface of the drive transmission member 222 toward a side (the Y2 side) opposite to the medical instrument 4 side.

Each of the drive transmission members 222 includes a fitting recess 222b, which is to be fitted with a fitting protrusion 75a of a corresponding one of the drivers 75 of the arm 60. The fitting recess 222b is provided at a surface of the drive transmission member 222 on the Y2 side (the arm 60 side) and is recessed from the Y2-side surface of the drive transmission member 222 toward the side (the Y1 side) opposite to the arm 60 side.

(Configuration of Manual Surgical Instrument)

The configuration of the manual surgical instrument 200 is described below. The manual surgical instrument 200 is originally an instrument manually operated by an operator such as a doctor. However, in a first embodiment, the manual surgical instrument 200 is not directly operated by the operator, but is operated by the medical manipulator 1 by using the remote control apparatus 2.

Figure 8:
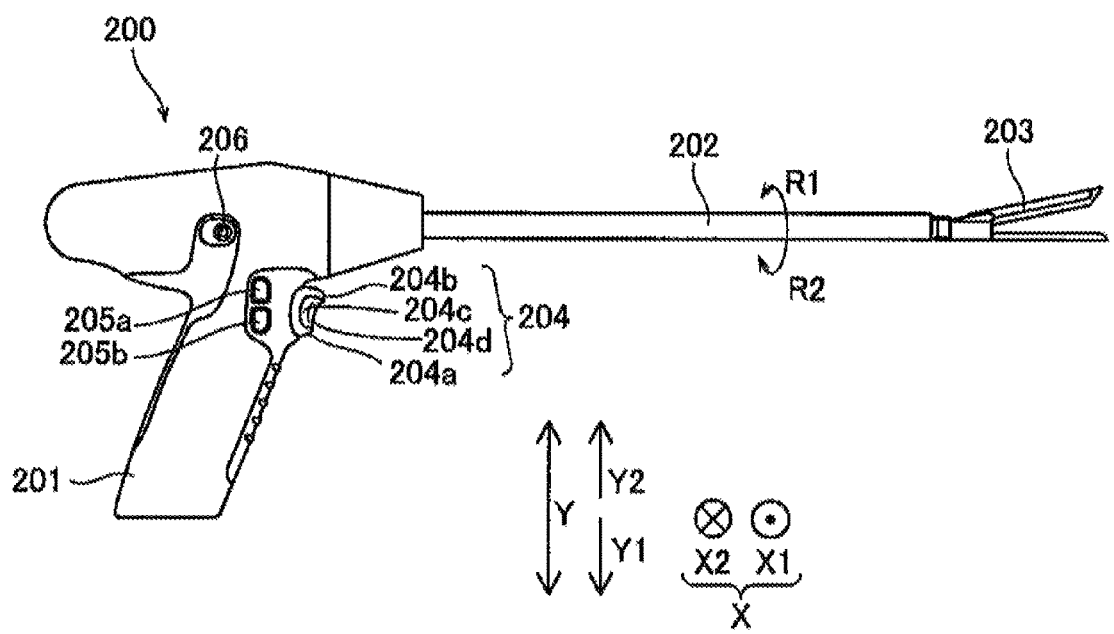
FIG. 8 is a diagram illustrating a view of a manual surgical instrument.

With reference to FIG. 8, the manual surgical instrument 200 to be attached to the arm 60 is described. The manual surgical instrument 200 can be attached to the robotic arm 60 instead of the robotic medical instrument 4 dedicated for the robotic arm 60. The manual surgical instrument 200 is configured to be driven by a battery. The manual surgical instrument 200 includes a grip portion 201, a shaft 202, and an end effector 203 that is provided at the distal end of the shaft 202. A cross key 204 is provided on a front surface of the grip portion 201 (the surface on the shaft 202 side). A pair of switch portions 205a and 205b and a switch portion 206 are provided on a side surface of the grip portion 201.

The switch portions 204, 205a, 205b, and 206 are buttons to be pressed by an operator such as a doctor. By pressing a Y1 side portion (a switch portion 204a) or a Y2 side portion (a switch portion 204b) of the cross key 204 by the operator, the end effector 203 is opened or closed. By pressing an X1 side portion (a switch portion 204c) or an X2 side portion (a switch portion 204d) of the cross key 204 by the operator, the end effector 203 is bent (swung) with respect to the shaft 202. By pressing one or the other of the pair of switch portions 205a and 205b by the operator, the end effector 203 rotates in the R1 direction or the R2 direction. By pressing the switch portion 206 by the operator, the mode is switched to the mode in which the skin of the patient P is to be sutured, for example, in a case where the manual surgical instrument 200 is a surgical stapler. After that, by continuously pressing the switch portion 204a or the switch portion 204b of the cross key 204, the operation of stitching by the stapler and the operation of cutting the vicinity of the sewn portion are performed.

(Configuration of Interface)

The interface 300 to be provided between the drivers 75 (the servo motors M2) provided to the holder 71 of the arm 60 and the manual surgical instrument 200 is described below.

Figure 9:
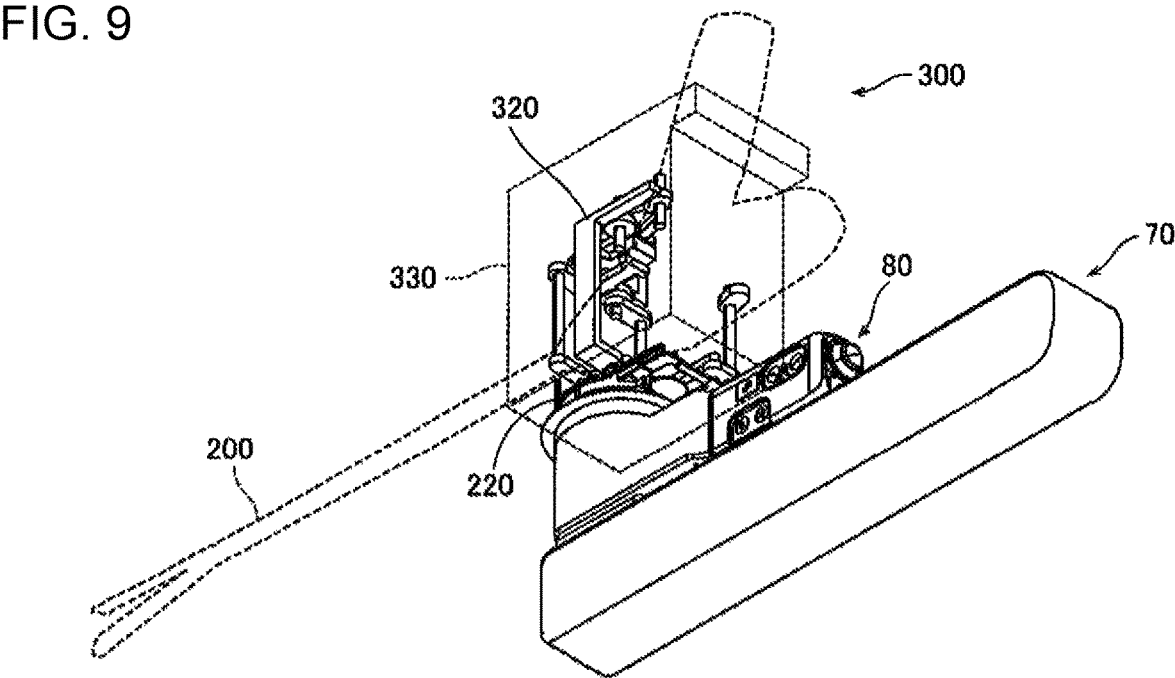
FIG. 9 is a diagram illustrating a view of the manual surgical instrument and an interface according to a first embodiment.

As illustrated in FIG. 9, the interface 300 is provided for operating the existing manual surgical instrument 200, which is to be manually operated by the operator, using the drivers 75 of the arm 60. In a first embodiment, the interface 300 includes the driven unit 320 (or driven device 320) and manipulation portions (321j, 321h, 322e, 322f, 323e, and 324d, see FIGS. 11 to 13). The interface 300 is configured to be fixed to the arm 60. Specifically, the interface 300 is fixed to the holder 71 of the translation movement mechanism 70 via the adaptor 220. The driven unit 320 is configured to be driven by driving forces transmitted from the drivers 75 (see FIG. 6) provided to the arm 60 via a connection portion 410 (see FIG. 17) of the interface 300. The manipulation portions are configured to operate the switch portions (204, 205a, 205b, and 206, see FIG. 8) of the manual surgical instrument 200 by the driving forces transmitted by the driven unit 320. Specifically, the manipulation portions are configured to be driven by the driving forces transmitted by the driven unit 320 so as to depress the switch portions (operation-target portions) of the manual surgical instrument 200. A detailed description thereof is given below.

Figure 10:
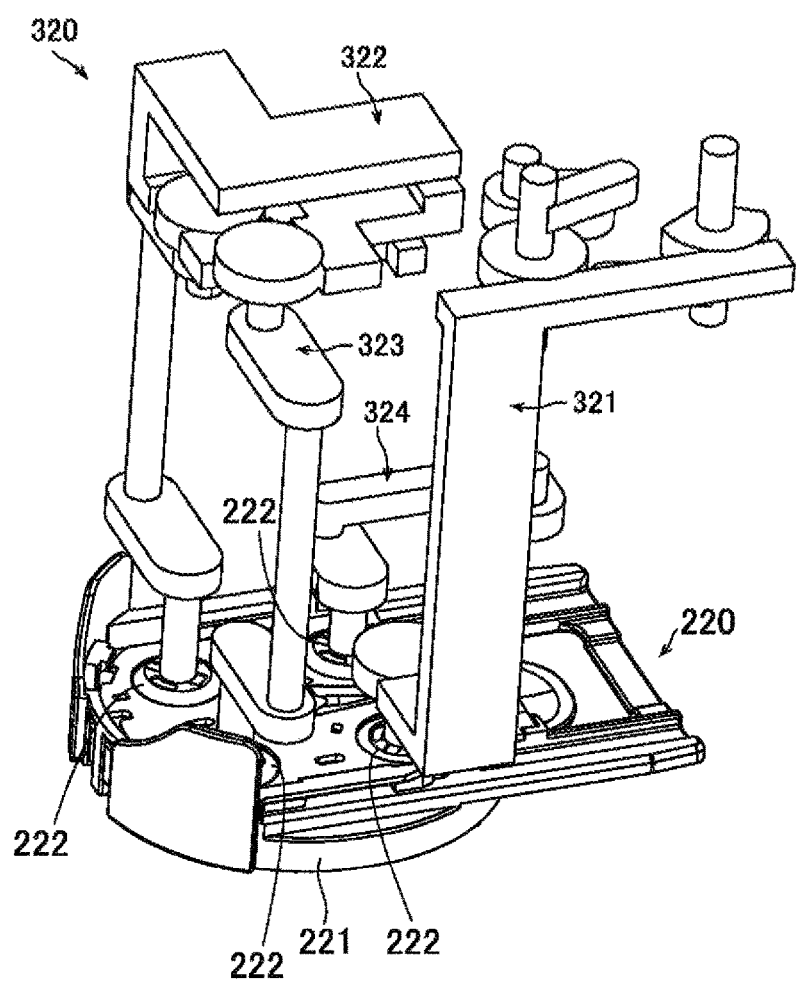
FIG. 10 is a diagram illustrating a view of a driven unit of the interface and the adaptor according to a first embodiment.

As illustrated in FIG. 10, the manual surgical instrument 200 (the interface 300) is detachably connected to the adaptor 220. The adaptor 220 is arranged between the holder 71 (the drivers 75) of the arm 60 and the manual surgical instrument 200.

Figure 11:
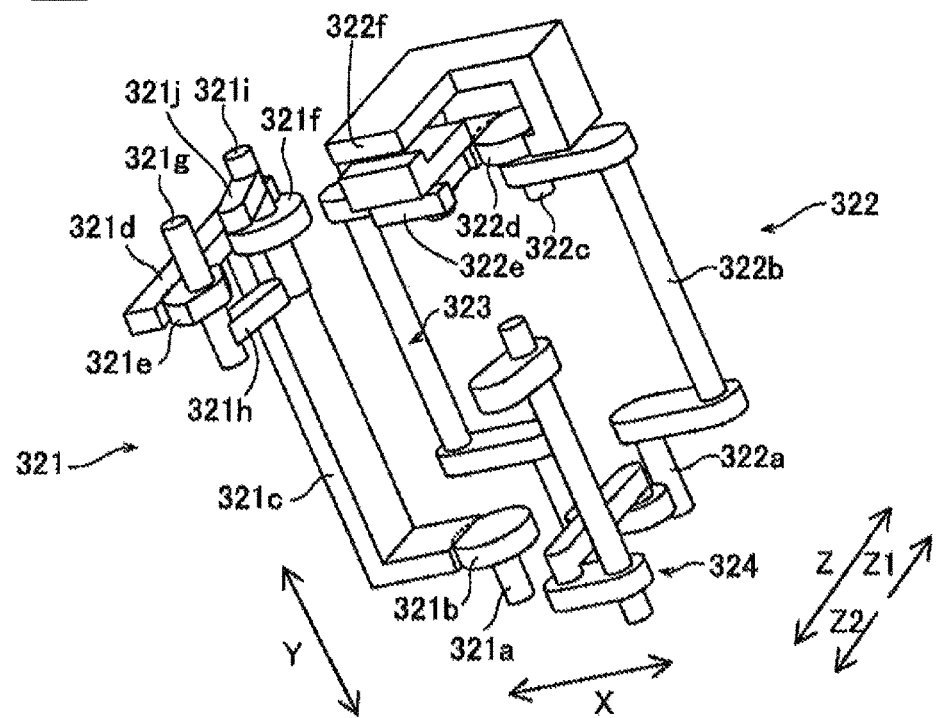
FIG. 11 is a diagram illustrating a view of the driven unit of the interface according to a first embodiment.
Figure 12:
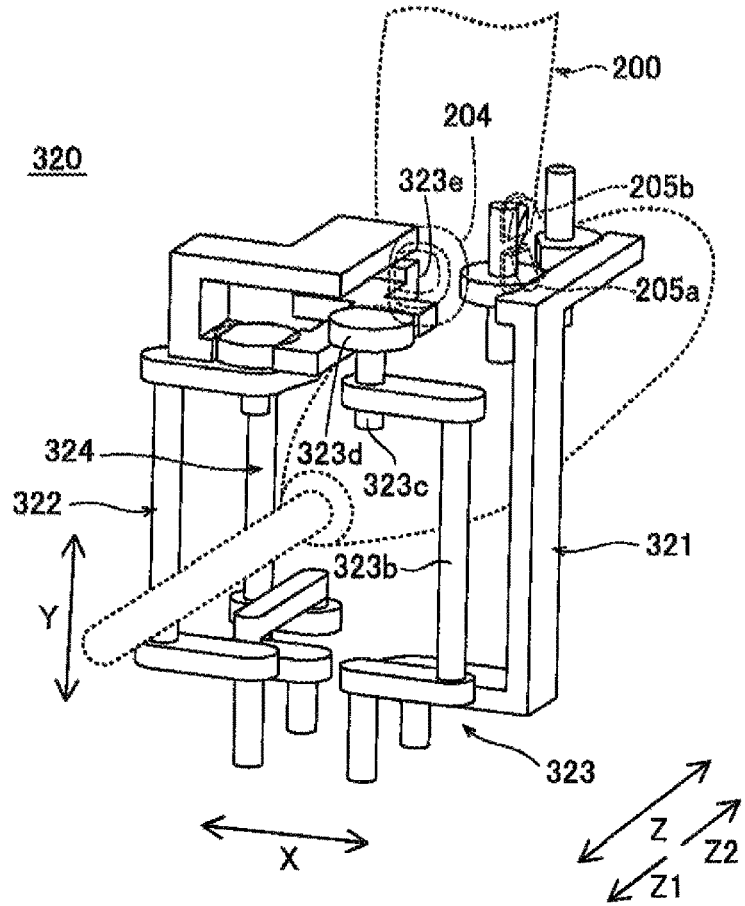
FIG. 12 is a diagram illustrating another view of the driven unit of the interface according to a first embodiment.
Figure 13:
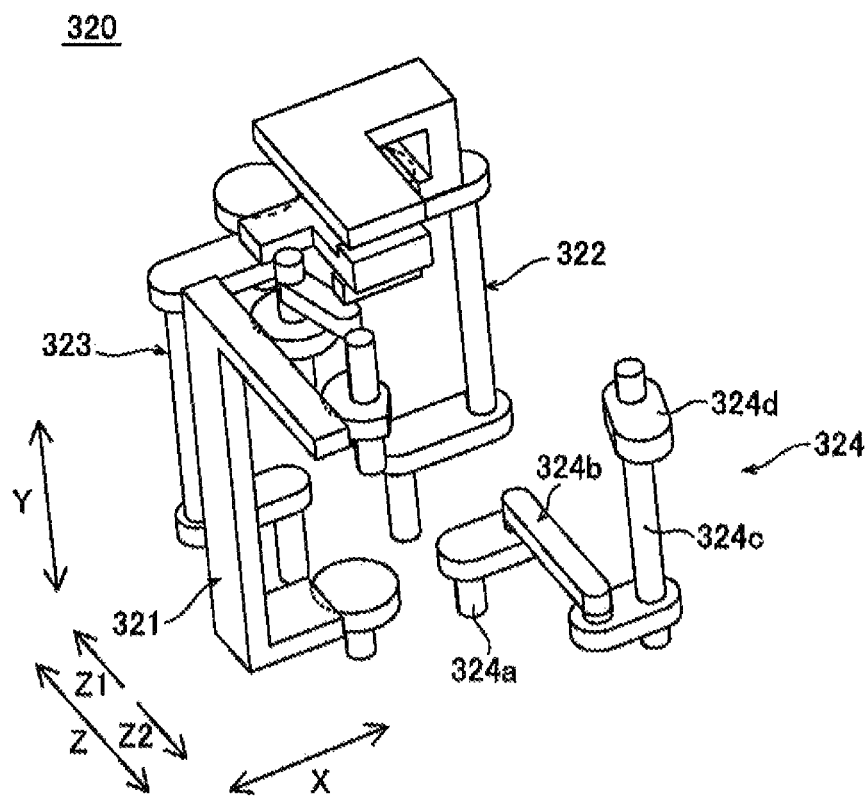
FIG. 13 is a diagram illustrating still another view of the driven unit of the interface according to a first embodiment.

As illustrated in FIGS. 11 to 13, the driven unit 320 is configured to be driven by the driving forces from the drivers 75 provided in the arm 60. Specifically, the driven unit 320 is connected to the drivers 75 via the drive transmission members 222 of the adaptor 220. In a first embodiment, the driven unit 320 includes at least one of a set of wires and a set of shafts. The driving forces of the drivers 75 are transmitted to the manipulation portions (321j, 321h, 322e, 322f, 323e, 324d) via the at least one of the set of wires and the set of shafts. In a first embodiment, the driven unit 320 is configured to transmit the driving forces of the drivers 75 to the manipulation portions (321j, 321h, 322e, 322f, 323e, 324d) via the set of shafts. A detailed description thereof is given below.

As illustrated FIG. 11, the driven unit 320 includes a driven part 321 to be driven by a corresponding one of the drive transmission members 222 (see FIG. 6) of the adaptor 220. The configuration of the driven part 321 is described below. The driven part 6321 includes a columnar shaft 321a extending along the Y direction to be connected to the drive transmission member 222, a gear 321b provided at the tip of the shaft 321a, and an L-shaped shaft 321c that meshes with the gear 321b. The shaft 321a is configured to be fitted into the fitting recess 222a (see FIG. 6) of the corresponding drive transmission member 222. Further, at the tip of the L-shaped shaft 321c, a columnar shaft 321d provided along the Z direction, and gears 321e and 321f that mesh with the columnar shaft 321d are provided.

The gear 321e is provided with a shaft 321g that penetrates the gear 321e. The shaft 321g is provided with a columnar manipulation portion 321h that extends along the X-Z plane and rotates along with the rotation of the shaft 321g. The gear 321f is provided with a shaft 321i that penetrates the gear 321f. The shaft 321i is provided with a columnar manipulation portion 321j that extends along the X-Z plane and rotates along with the rotation of the shaft 321i. The manipulation portion 321h is driven to press the switch portion 205a (see FIG. 8) of the manual surgical instrument 200, when the corresponding drive transmission member 222 of the adaptor 220 is rotated to one side. The manipulation portion 321j is driven to press the switch portion 205b of the manual surgical instrument 200, when the corresponding drive transmission member 222 of the adaptor 220 is rotated to the other side.

Further, as illustrated in FIG. 11, the driven unit 320 includes a driven part 322 to be driven by a corresponding one of the drive transmission members 222 (see FIG. 6) of the adaptor 220. The configuration of the driven part 322 is described below. The driven part 322 is provided with a columnar shaft 322a connected to the drive transmission member 222 and extending along the Y direction and a U-shaped shaft 322b provided at the tip of the shaft 322a. The shaft 322a is configured to be fitted into the fitting recess 222a (see FIG. 6) of the corresponding drive transmission members 222. The U-shaped shaft 322b is provided with a shaft 322c extending along the Y direction. The shaft 322c is provided with a gear 322d that rotates along with the rotation of the shaft 322c. On one side of the gear 322d in the X direction, a manipulation portion 322e that meshes with the gear 322d and extends toward the cross key 204 (switch portion 204b) is provided. On the other side of the gear 322d in the X direction, a manipulation portion 322f extending toward the cross key 204 (switch portion 204a) is provided. The manipulation portion 322e is driven to press the cross key 204 (the switch portion 204b), when the gear 322d is rotated to one side by the corresponding drive transmission member 222 of the adaptor 220 being rotated to the one side. The manipulation portion 322f is driven to press the cross key 204 (the switch portion 204a), when the gear 322d is rotated to the other side by the corresponding drive transmission member 222 of the adaptor 220 being rotated to the other side.

As illustrated FIG. 12, the driven unit 320 includes a driven part 323 to be driven by a corresponding one of the drive transmission members 222 of the adaptor 220. The configuration of the driven part 323 is described below. The driven part 323 is provided with a columnar shaft 323a extending along the Y direction to be connected to the corresponding drive transmission member 222 and a U-shaped shaft 323b provided at the tip of the shaft 323a. The shaft 323a is configured to be fitted into the fitting recess 222a (see FIG. 6) of the corresponding drive transmission member 222. The U-shaped shaft 323b is provided with a shaft 323c extending along the Y direction and a gear 323d that rotates with the rotation of the shaft 323c. The gear 323d is provided with a manipulation portion 323e that meshes with the gear 323d and extends toward the cross key 204 (the switch portion 204c, the switch portion 204d). When the gear 323d is rotated to one side by the corresponding drive transmission member 222 of the adaptor 220 being rotated to the one side, the manipulation portion 323e is driven to move to one side in the X direction. As a result, the manipulation portion 323e presses the cross key 204 so that the cross key 204 is inclined to the one side in the X direction. As a result, the switch portion 204c is pressed. When the gear 323d is rotated to the other side in the rotational direction thereof by the corresponding drive transmission member 222 of the adaptor 220 being rotated to the other side, the manipulation portion 323e is driven to move to the other side in the X direction. As a result, the manipulation portion 323e presses the cross key 204 so that the cross key 204 is inclined to the other side in the X direction. As a result, the switch portion 204d is pressed.

As illustrated in FIG. 13, the driven unit 320 includes a driven part 324 to be driven by a corresponding one of the drive transmission members 222 (see FIG. 6) of the adaptor 220. The configuration of the driven part 324 is explained below. The driven part 324 is provided with a columnar shaft 324a extending along the Y direction to be connected to the drive transmission member 222, and a link portion 324b provided at the tip of the shaft 324a. The shaft 324a is configured to fit into the fitting recess 222a (see FIG. 6) of the corresponding drive transmission member 222. Further, the link portion 324b is provided with a shaft 324c extending along the Y direction. The shaft 324c is provided with a manipulation portion 324d that rotates along with the rotation of the shaft 324c. When the corresponding drive transmission member 222 of the adaptor 220 is rotated, the shaft 324c is rotated. Thus, the manipulation portion 324d is rotated with the rotation of the shaft 324c. As a result, the switch portion 206 (see FIG. 8) is pressed.

As described above, in a first embodiment, the plurality of the manipulation portions (321j, 321h, 322e, 322f, 323e, 324d) are provided to correspond to the plurality of the switch portions (204, 205a, 205b, 206) provided in the manual surgical instrument 200.

Figure 14:
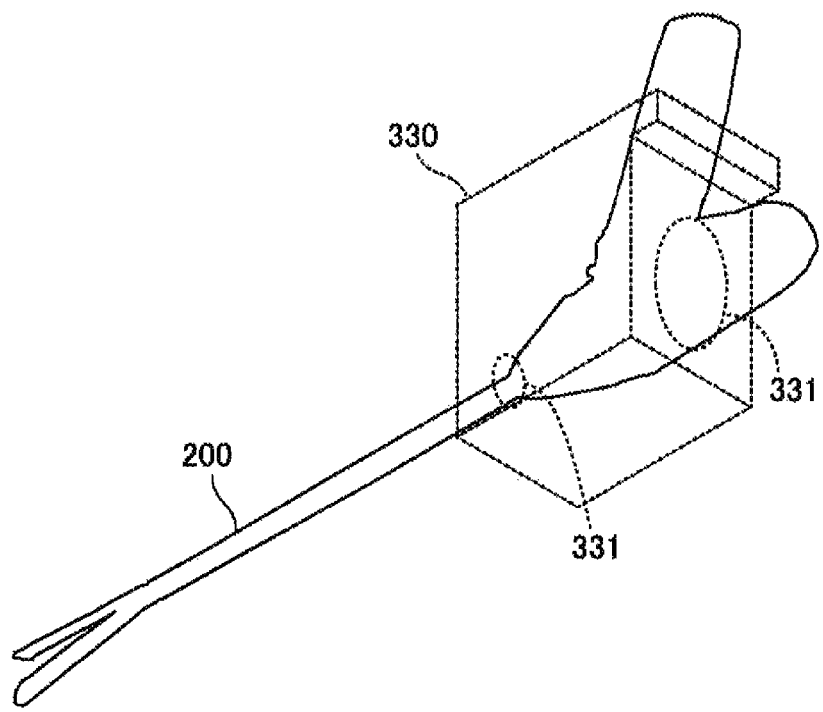
FIG. 14 is a diagram illustrating a view of the manual surgical instrument and the interface (housing) according to a first embodiment.

In a first embodiment, as illustrated in FIG. 14, the interface 300 includes a housing 330 that accommodates therein the driven unit 320 and the manipulation portions (321j, 321h, 322e, 322f, 323e, 324d) and holds the manual surgical instrument 200 in such a manner that the housing 330 positions the switch portions of the manual surgical instrument 200 with respect to the manipulation portions of the interface 300. Specifically, portions of the manual surgical instrument 200 are inserted in holes 331 provided to the housing 330, so that the manual surgical instrument 200 is held by the housing 330. As a result, the manual surgical instrument 200 is held in a state of being positioned with respect to the manipulation portions.

(Configuration of Control Unit of Medical Manipulator)

Figure 15:
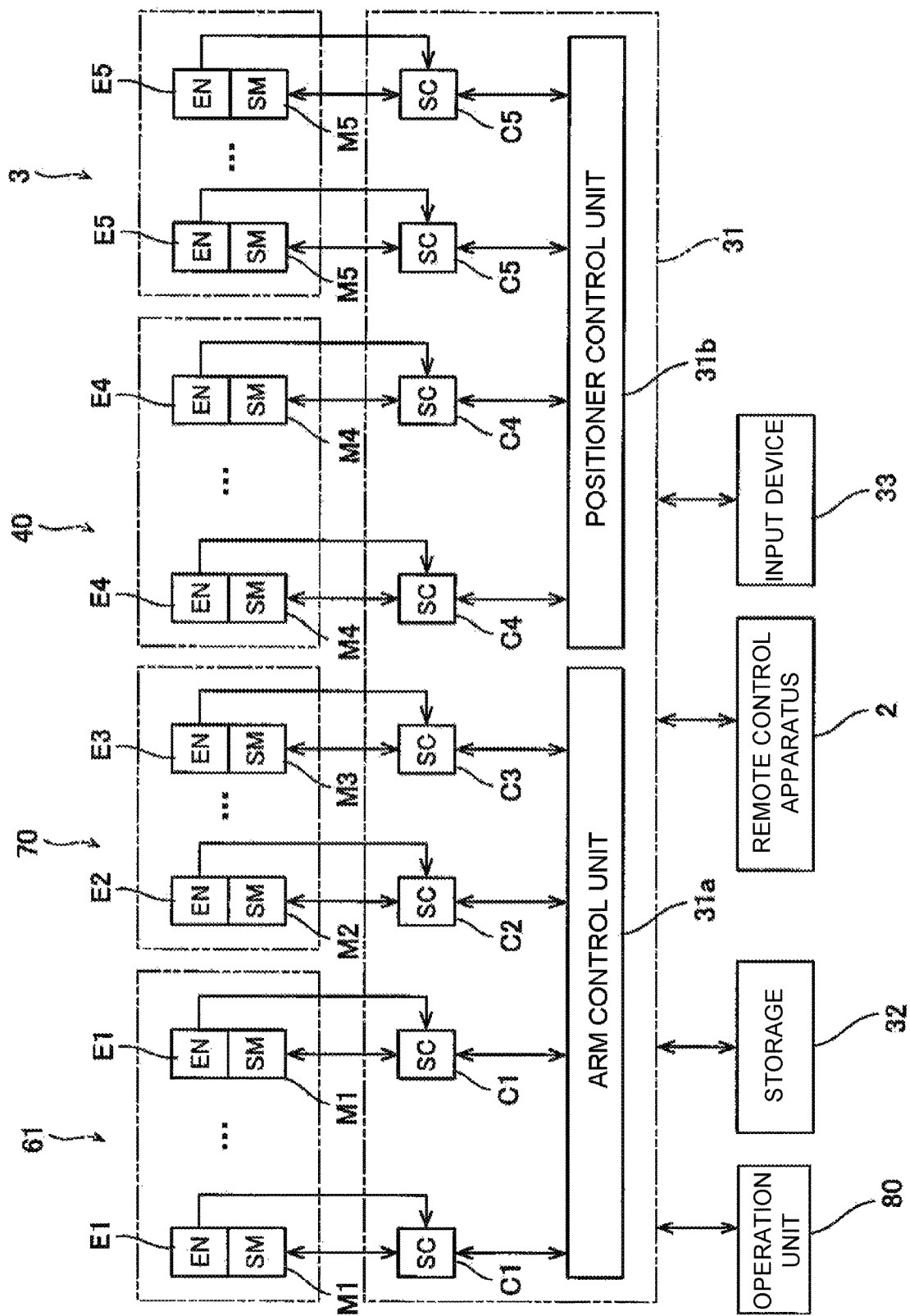
FIG. 15 is a block diagram of a configuration of a control unit of the medical manipulator according to a first embodiment.

As illustrated in FIG. 15, the arm 60 is provided with a plurality of servomotors M1, a plurality of encoders E1, and a plurality of speed reducers (not illustrated), so as to correspond to the plurality of joints 64 of the arm section 61. The encoders E1 are configured to detect the rotation angles of the servomotors M1. The speed reducers are configured to reduce the rotations of the servomotors M1 to increase the torques thereof.

As illustrated in FIG. 15, the translation movement mechanism 70 includes the servomotors M2 for rotating the rotors (rotation members) provided in the drive unit 4a of the medical instrument 4, a servomotor M3 for translationally moving the medical instrument 4, encoders E2 and E3, and speed reducers (not illustrated). The encoders E2 and E3 are configured to detect the rotation angles of the servomotors M2 and M3, respectively. The speed reducers are configured to reduce the rotations of the servomotors M2 and M3 to increase the torques thereof.

The positioner 40 is provided with a plurality of servomotors M4, a plurality of encoders E4, and a plurality of speed reducers (not illustrated), so as to correspond to the plurality of joints 43 of the positioner 40. The encoders E4 are configured to detect the rotation angles of the servomotors M4. The speed reducers are configured to reduce the rotations of the servomotors M4 to increase the torques thereof.

The medical trolley 3 is provided with servomotors M5 that drive a plurality of front wheels (not illustrated) of the medical trolley 3 respectively, encoders E5, and speed reducers (not illustrated). The encoders E5 are configured to detect the rotation angles of the servomotors M5. The speed reducers are configured to reduce the rotations of the servomotors M5 to increase the torques thereof.

The control unit 31 of the medical trolley 3 includes an arm control unit 31a that controls the movements of the plurality of arms 60 based on commands, and a positioner control unit 31b that controls the movement of the positioner 40 and driving of the front wheels (not illustrated) of the medical trolley 3 based on commands. Servo control units C1 that control the servo motors M1 for driving the arm 60 are electrically connected to the arm control unit 31a. Further, the encoders E1 that detect the rotation angles of the servomotors M1 are electrically connected to the servo control units C1, respectively.

Servo control units C2 that control the servomotors M2 (the drivers 75) that drive the medical instrument 4 or the manual surgical instrument 200 are electrically connected to the arm control unit 31a. The encoders E2 that detect the rotation angles of the servomotors M2 are electrically connected to the servo control units C2, respectively. A servo control unit C3 that controls the servomotor M3 for translationally moving by the translational movement mechanism 70 is electrically connected to the arm control unit 31a. The encoder E3 for detecting the rotation angle of the servomotor M3 is electrically connected to the servo control unit C3.

The operation command inputted to the remote control apparatus 2 is inputted to the arm control unit 31a. The arm control unit 31a generates position commands based on the operation command inputted and the rotation angles detected by the encoders E1 (E2, E3), and outputs the position commands to the servo control units C1 (C2, C3). The servo control units C1 (C2, C3) generate torque commands based on the position commands inputted from the arm control unit 31a and the rotation angles detected by the encoders E1 (E2, E3), and output the torque commands to the servomotors M1 (M2, M3). As a result, the arm 60 is moved so as to comply with the operation command inputted to the remote control apparatus 2.

The control unit 31 (arm control unit 31a) is configured to operate the arm 60 based on an input signal from the joystick 82 of the arm operation unit 80. Specifically, the arm control unit 31a generates position commands based on the input signal (operation command) inputted from the joystick 82 and the rotation angles detected by the encoders E1, and outputs the position commands to the servo control units C1. The servo control units C1 generate torque commands based on the position commands inputted from the arm control unit 31*a* and the rotation angles detected by the encoders E1, and output the torque commands to the servomotors M1. As a result, the arm 60 is moved so as to follow the operation command inputted to the joystick 82.

The control unit 31 (arm control unit 31*a*) is configured to operate the arm 60 based on an input signal from the switch section 83 of the arm operation unit 80. Specifically, the arm control unit 31*a* generates position commands based on the input signal (operation command) inputted from the switch section 83 and the rotation angles detected by the encoders E1 or E3, and outputs the position commands to the servo control units C1 or C3. The servo control units C1 or C3 generate torque commands based on the position commands inputted from the arm control unit 31*a* and the rotation angles detected by the encoders E1 or E3, and output the generated torque commands to the servomotors M1 or M3. As a result, the arm 60 is moved so as to follow the operation command inputted to the switch section 83.

As illustrated in FIG. 15, the servo control units C4 that control the servomotors M4 for moving the positioner 40 are electrically connected to the positioner control unit 31*b*. The encoders E4 that detect the rotation angles of the servomotors M4 are electrically connected to the servo control units C4. The servo control units C5 that control the servomotors 5 for driving the front wheels (not illustrated) of the medical trolley 3 are electrically connected to the positioner control unit 31*b*. The encoders E5 that detect the rotation angles of the servomotors M5 are electrically connected to the servo control units C5.

An operation command regarding setting of the preparation position and the like is inputted from the input device 33 to the positioner control unit 31*b*. The positioner control unit 31*b* generates position commands based on the operation command inputted from the input device 33 and the rotation angles detected by the encoders E4, and outputs the position commands to the servo control units C4. The servo control units C4 generate torque commands based on the position commands inputted from the positioner control unit 31*b* and the rotation angles detected by the encoders E4, and output the torque commands to the servomotors M4. As a result, the positioner 40 is moved so as to follow the operation command inputted to the input device 33. Similarly, the positioner control unit 31*b* moves the medical trolley 3 based on the operation command from the input device 33.

(Advantageous Effects of First Embodiment)

In a first embodiment, the following advantageous effects can be obtained.

In a first embodiment, as described above, the interface 300 is provided with the driven unit 320 to be driven by the driving forces transmitted from the drivers 75 provided in the arm 60 and the manipulation portions (321*j*, 321*h*, 322*e*, 322*f*, 323*e*, 324*d*) for operating the switch portions (204, 205*a*, 205*b*, 206) of the surgical instrument 200. As a result, the switch portions (operation-target portions) of the manual surgical instrument 200 can be operated by the manipulation portions of the interface 300 being driven (moved) by the driving forces of the drivers 75 provided in the arm 60. As a result, the existing manual surgical instrument 200 can be operated without using the surgical instrument 4 dedicated for the robotic arm 60 (the robotic surgical instrument 4). Further, in a first embodiment, since the interface 300 includes the housing 330 configured to hold the manual surgical instrument 200 with positioning the manual surgical instrument 200 with respect to the manipulation portions of the interface 300, the switch portions (operation-target portions) of the manual surgical instrument 200 are positioned with respect to the manipulation portions of the interface 300. Therefore, the manual surgical instrument 200 can be easily attached to the housing 330.

Further, in a first embodiment, as described above, the interface 300 that connects the drivers 75 of the robotic arm 60 and the manual surgical instrument 200 provided with the switch portions (204, 205*a*, 205*b*, 206) is configured such that the manipulation portions (321*j*, 321*h*, 322*e*, 322*f*, 323*e*, 324*d*) of the interface 300 are driven to press the switch portions by the driving forces transmitted through the driven unit 320 of the interface 300 from the drivers 75. As a result, the switch portions (operation-target portions) of the manual surgical instrument 200 can be easily pressed by the manipulation portions of the interface 300 being driven (moved) by the driving forces transmitted through the driven unit 320 of the interface 300, so that the existing manual surgical instrument 200 can be easily operated.

Further, in a first embodiment, as described above, the interface 300 that connects the drivers 75 of the robotic arm 60 and the manual surgical instrument 200 provided with the plurality of switch portions (204, 205*a*, 205*b*, and 206) includes the plurality of manipulation portions (321*j*, 321*h*, 322*e*, 322*f*, 323*e*, and 324*d*) corresponding to the plurality of switch portions of the manual surgical instrument 200. As a result, even when the manual surgical instrument 200 is provided with the plurality of switch portions, the existing manual surgical instrument 200 can be operated by the plurality of manipulation portions.

Further, in a first embodiment, as described above, the driven unit 320 includes the plurality of shafts and is configured to transmit the driving forces of the drivers 75 to the manipulation portions (321*j*, 321*h*, 322*e*, 322*f*, 323*e*, and 324*d*) via the plurality of shafts. Therefore, the driving forces of the drivers 75 provided in the arm 60 can be easily transmitted to the manipulation portions via the plurality of shafts.

Further, in a first embodiment, as described above, the driven unit 320 transmits the driving forces transmitted from the drivers 75, to the manipulation portions (321*j*, 321*h*, 322*e*, 322*f*, 323*e*, and 324*d*) through the shafts of the driven unit 320. As a result, the configuration of the unit 320 can be simplified, since the driving forces of the drivers 75 are directly transmitted to the manipulation portions via the shafts, unlike a case where a speed reduction unit for decelerating the driving forces of the drivers 75 or the like is provided.

Second Embodiment

Next, an interface 400 according to a second embodiment is described with reference to FIGS. 16 to 20. In the interface 400 according to a second embodiment, a driven unit 420 includes wires and shafts.

In a second embodiment, as illustrated in FIGS. 16 to 20, the driven unit 420 is configured in such a manner that one ends of the wires are wound around the drivers 75 and the other ends of the wires are wound around the shafts, so that manipulation portions are driven to operate the switch portions (204, 205*a*, 205*b*, and 206, see FIG. 8) by winding the wires. A detailed description thereof is given below.

Figure 16:
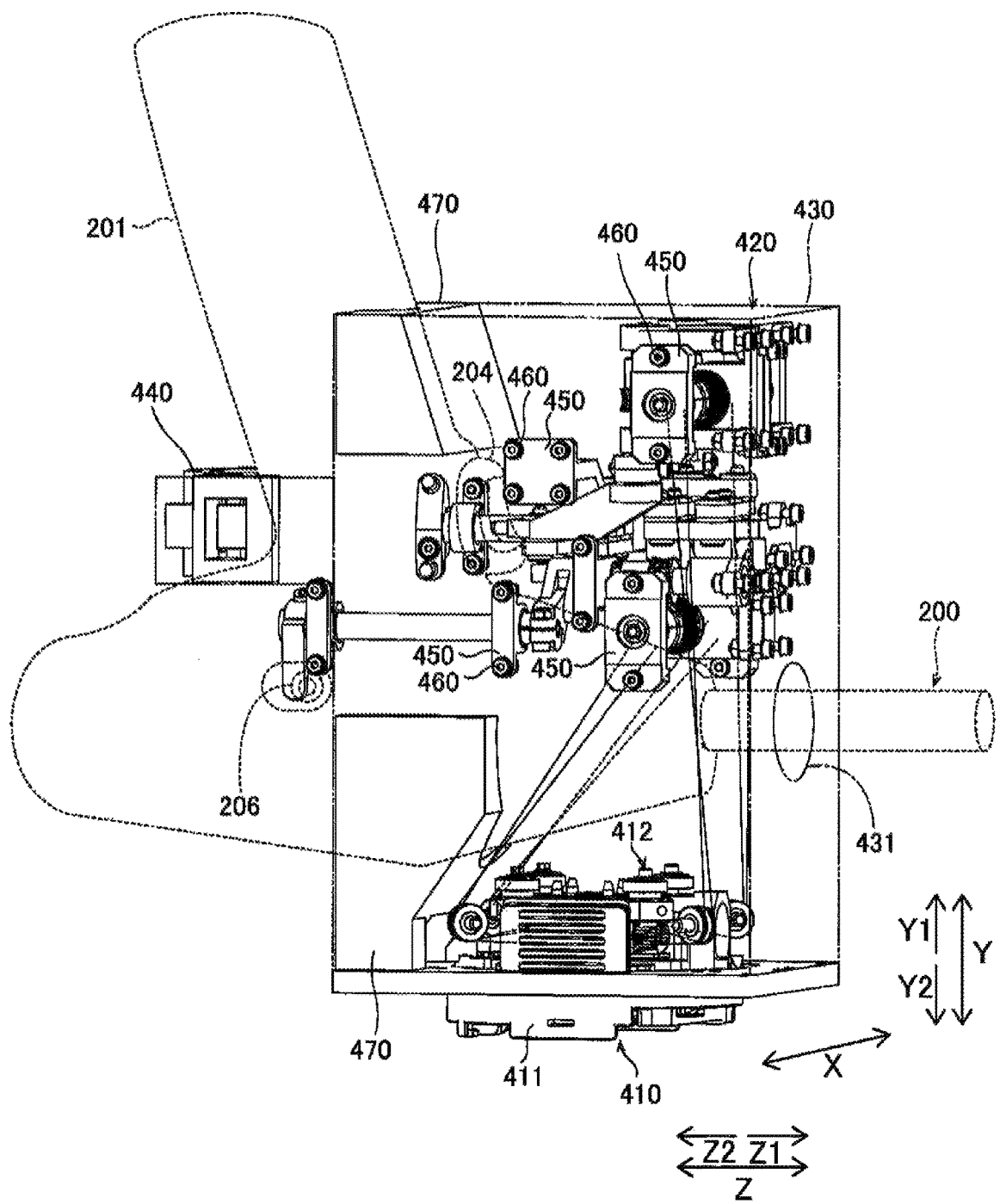
FIG. 16 is a diagram illustrating a view of a manual surgical instrument and an interface according to a second embodiment.
Figure 17:
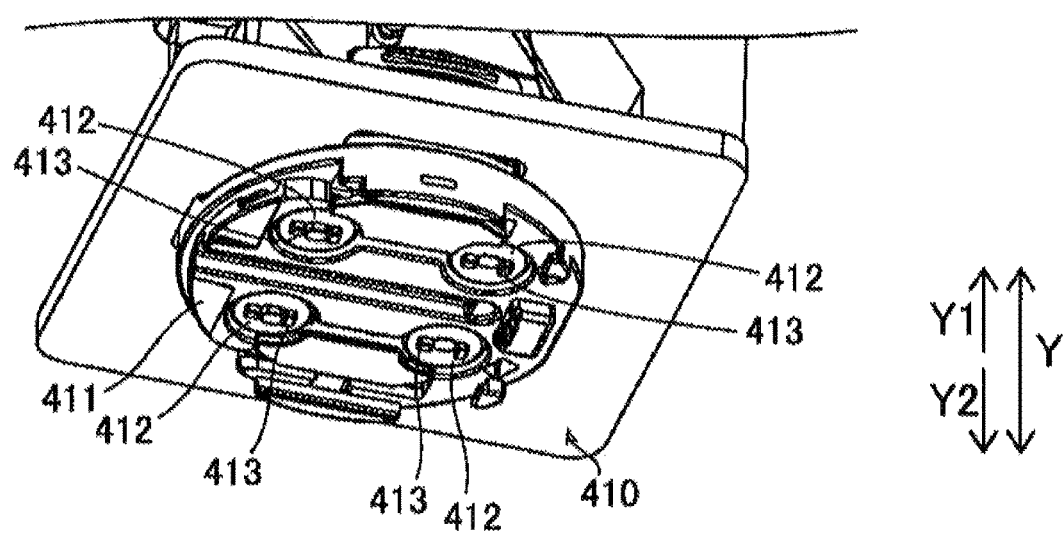
FIG. 17 is a diagram illustrating a perspective view of the interface as seen from the Y2 side according to a second embodiment.

The interface 400 includes a connection portion 410, as illustrated in FIGS. 16 and 17. The connection portion 410 is attached to and thus connected to the arm 60 via the adaptor 220. The connection portion 410 includes a connection portion main body 411. Drive transmission members 412, to which the driving forces from the arm 60 are transmitted via the drive transmission members 222 of the adaptor 220, are rotatably provided in the connection unit main body 411. Each of the drive transmission member 412 is provided with a fitting projection 413 that is to be fitted in the fitting recess 222a of a corresponding one of the drive transmission member 222.

Figure 18:
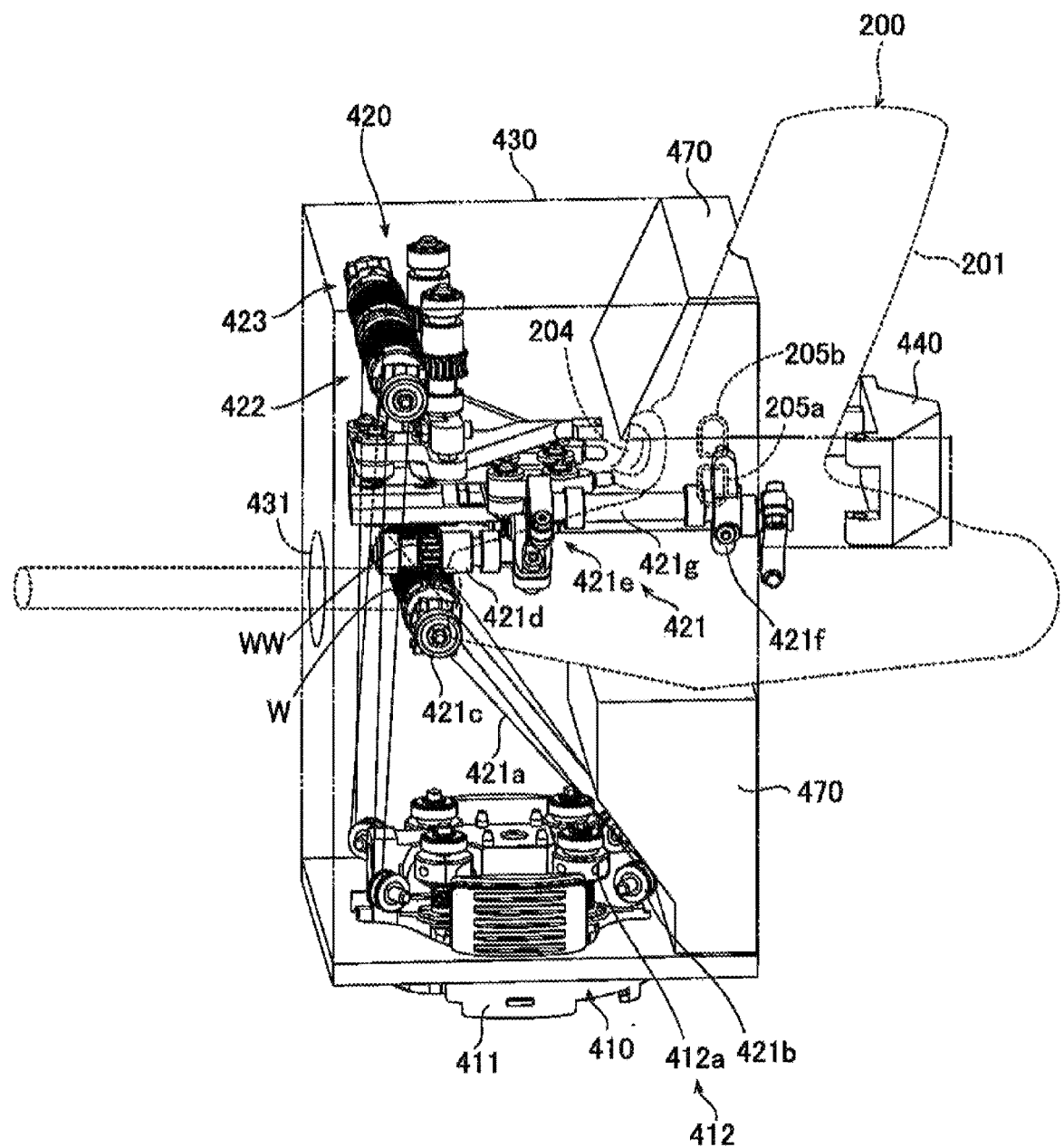
FIG. 18 is a diagram illustrating a view of a driven unit of the interface according to a second embodiment.

As illustrated in FIG. 18, the driven unit 420 includes a first driven part 421. The configuration of the first driven part 421 is described below. The first driven part 421 includes one (412a) of the drive transmission members 412. The first driven part 421 is provided with wires 421a whose one ends are connected to the drive transmission member 412a. The other ends of the wires 421a are connected to the shaft 421c via a pulley 421b. The wires 421a are composed of two wires. One of the two wires 421a rotates the shaft 421c toward one side, when the drive transmission member 412a is rotated to one side. The other of the two wires 421a rotates the shaft 421c toward the other side opposite to the one side, when the drive transmission member 412a is rotated to the other side. A shaft 421d is provided orthogonal to the shaft 421c. The shaft 421c is provided with a worm W, and the shaft 421d is provided with a worm wheel WW. Accordingly, in a second embodiment, the first driven part 421 is configured to decelerate the rotational drive (rotational speed) from the driver 75 of the arm 60 by the worm W and the worm wheel WW. The worm W and the worm wheel WW are examples of a speed reduction unit.

The shaft 421d is provided with a link mechanism 421e. The link mechanism 421e is provided with a manipulation portion 421f. When the drive transmission member 412a is rotated to one side, the shaft 421g of the link mechanism 421e is rotated to the one side and thus the manipulation portion 421f is rotated to the one side along with the rotation of the shaft 421g. As a result, the switch portion 205a is pressed. When the drive transmission member 412a is rotated to the other side, the shaft 421g of the link mechanism 421e is rotated to the other side and thus the manipulation portion 421f is rotated to the other side along with the rotation of the shaft 421g. As a result, the switch portion 205b is pressed.

Figure 19:
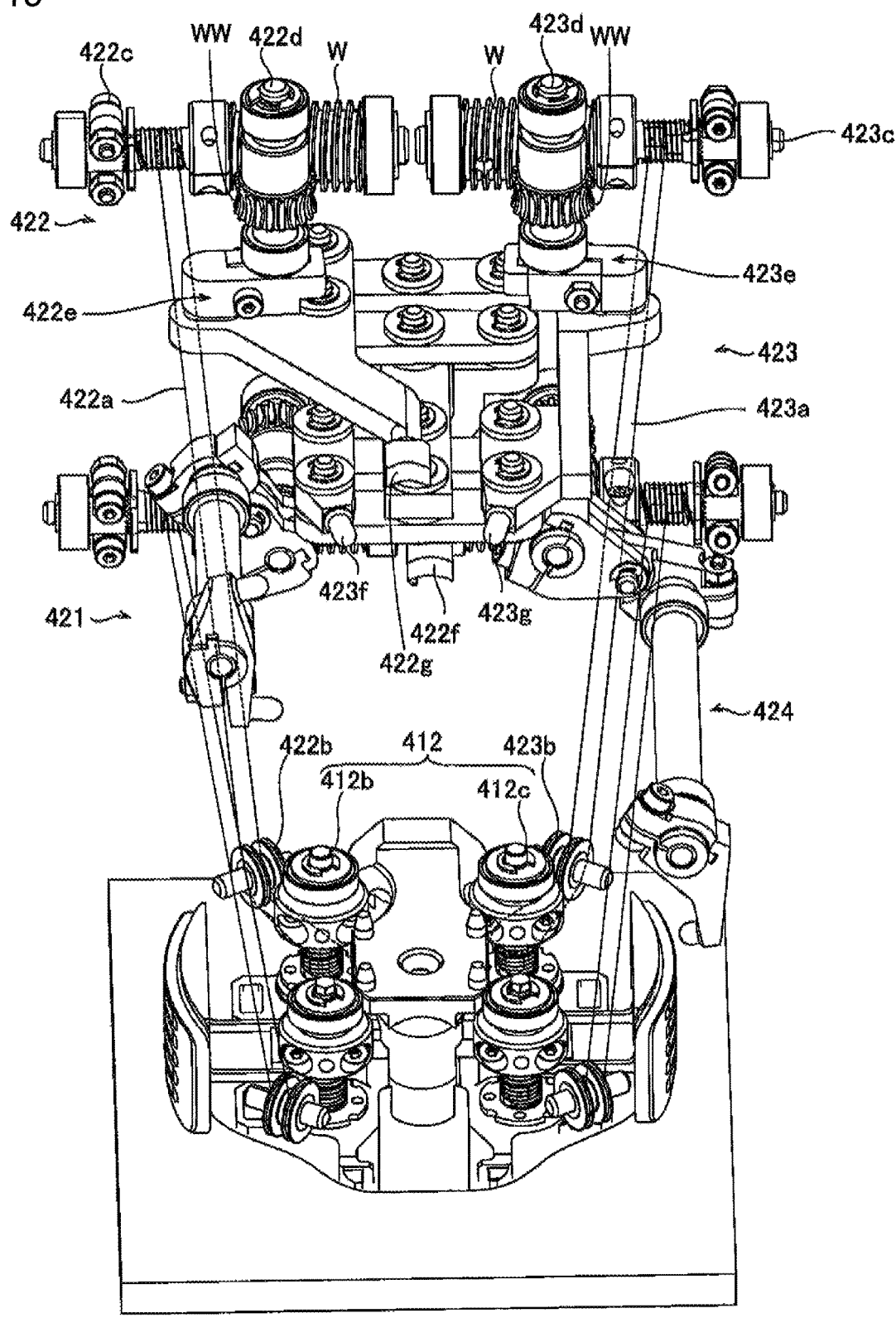
FIG. 19 is a diagram illustrating another view of the driven unit of the interface according to a second embodiment.

As illustrated in FIG. 19, the driven unit 420 includes a second driven part 422. The configuration of the second driven part 422 is described below. The second driven part 422 includes one (412b) of the drive transmission members 412. The second driven part 422 is provided with wires 422a whose one ends are connected to the drive transmission member 412b. The other ends of the wires 422a are connected to the shaft 422c via a pulley 422b. The wires 422a are composed of two wires. One of the wires 422a rotates the shaft 422c to one side, when the drive transmission member 412b is rotated to one side. The other of the wires 422a rotates the drive transmission member 412b to the other side opposite to the one side, when the shaft 422c is rotated to the other side. A shaft 422d is provided orthogonal to the shaft 422c. The shaft 422c is provided with a worm W. The shaft 422d is provided with a worm wheel WW. Accordingly, in a second embodiment, the second driven part 422 is configured to decelerate the rotational drive (rotational speed) from the driver 75 of the arm 60 by the worm W and the worm wheel WW.

The shaft 422d is provided with a parallel link mechanism 422e. The parallel link mechanism 422e is provided with a plurality of manipulation portions 422f and 422g. By rotating the drive transmission member 412b to one side, the manipulation portion 422f moves toward the switch portion 204b of the cross key 204. As a result, the switch portion 204b is pressed by the manipulation portion 422f. By rotating the drive transmission member 412b to the other side, the manipulation portion 422g moves toward the switch portion 204a of the cross key 204. As a result, the switch portion 204a is pressed by the manipulation portion 422g.

As illustrated in FIG. 19, the driven unit 420 includes a third driven part 423. Hereinafter, the configuration of the third driven part 423 is described. The third driven part 423 includes one (412c) of the drive transmission members 412. The third driven part 423 is provided with wires 423a whose one ends are connected to the drive transmission member 412c. The other ends of the wires 423a are connected to the shaft 423c via a pulley 423b. The wires 423a are composed of two wires. One of the wires 423a rotates the shaft 423c to one side when the drive transmission member 412c is rotated to one side, and the other of the wires 423a rotates the shaft 423c to the other side opposite to one side, when the drive transmission member 412c is rotated to the other side. A shaft 423d is provided orthogonal to the shaft 423c. The shaft 423c is provided with a worm W. The shaft 423d is provided with a worm wheel WW. Therefore, in a second embodiment, third driven part 423 is configured to decelerate the rotational drive (rotational speed) from the driver 75 of the arm 60 by the worm W and the worm wheel WW.

In a second embodiment, the shaft 423d is provided with a parallel link mechanism 423e. The parallel link mechanism 423e is provided with a plurality of manipulation portions 423f and 423g.

By rotating the drive transmission member 412c to one side, the manipulation portion 423f moves toward the switch portion 204c of the cross key 204. As a result, the switch portion 204c is pressed by the manipulation portion 423f. By rotating the drive transmission member 412c to the other side, the manipulation portion 423g moves toward the switch portion 204d of the cross key 204. As a result, the switch portion 204d is pressed by the manipulation portion 423g.

Figure 20:
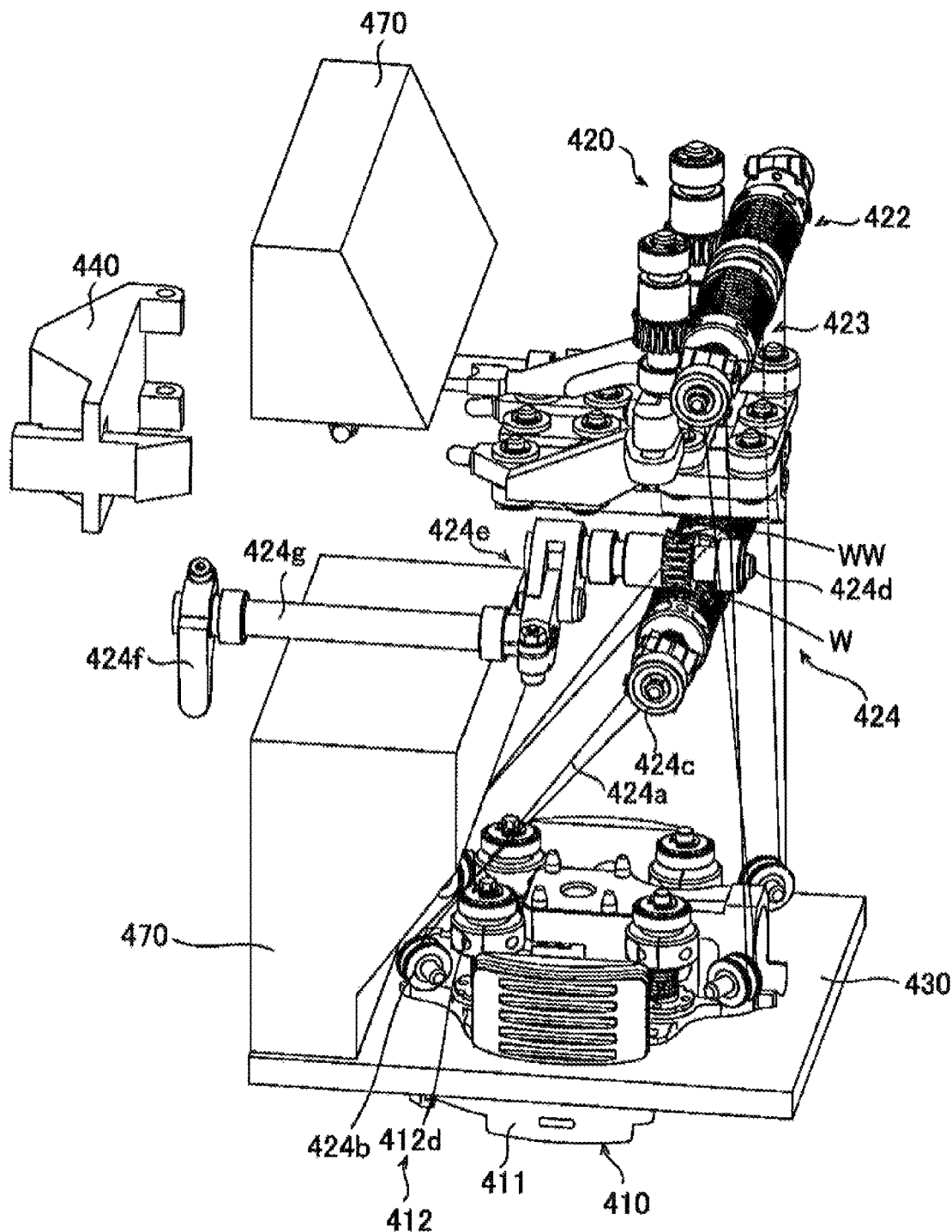
FIG. 20 is a diagram illustrating still another view of the driven unit of the interface according to a second embodiment.

As illustrated in FIG. 20, the driven unit 420 includes a fourth driven part 424. The configuration of the fourth driven part 424 is described below. The fourth driven part 424 includes one (412d) of the drive transmission members 412. The fourth driven part 424 is provided with wires 424a whose one ends are connected to the drive transmission member 412d. The other ends of the wires 424a are connected to the shaft 424c via a pulley 424b. The wires 424a are composed of two wires. One of the wires 424a rotates the shaft 424c to one side when the drive transmission member 412d is rotated to one side. The other of the wires 424a rotates the shaft 424c to the other side opposite to the one side, when the drive transmission member 412d is rotated to the other side. A shaft 424d is provided orthogonal to the shaft 424c. The shaft 424c is provided with a worm W, and the shaft 424d is provided with a worm wheel WW. Accordingly, in a second embodiment, the fourth driven part 424 is configured to reduce the rotational drive (rotational speed) from the driver 75 of the arm 60 by the worm W and the worm wheel WW. The worm W and the worm wheel WW of the fourth driven part 424 are examples of a speed reduction unit.

The shaft 424d is provided with a link mechanism 424e. The link mechanism 424e is provided with a manipulation portion 424f. By rotating the drive transmission member 412d, the shaft 424g of the link mechanism 424e is rotated. Thus, the manipulation portion 424f is rotated with the rotation of the shaft 424g. As a result, the switch portion 206 is pressed.

In a second embodiment, as illustrated in FIGS. 16 and 18, the interface 400 includes a housing 430 that houses therein the connection portion 410, the driven unit 420 and the manipulation portions (421f, 422f, 422g, 423f, 423g, 424f) and holds the manual surgical instrument 200 with positioning the manual surgical instrument 200 with respect to the driven unit 420 and the manipulation portions. Specifically, the manual surgical instrument 200 is inserted into a hole 431 of the housing 430. The interface 400 includes a lock member 440 for fixing the manual surgical instrument 200 positioned with respect to the manipulation portions. The lock member 440 is configured to lock the grip portion 201 of the manual surgical instrument 200. The lock member 440 is fixed to the housing 430. The housing 430 is an example of a surgical instrument holder.

As illustrated in FIG. 16, the driven unit 420 is provided with plural mounting plates 450. The driven unit 420 is fixed to the housing 430 by screwing the plural mounting plates 450 to the housing 430 with screws 460. Note that in FIGS. 18 to 20, the mounting plates 450 are omitted (not illustrated) in order to facilitate understanding of the configuration of the driven unit 420. Plural spacers 470 are provided between the manual surgical instrument 200 and the housing 430 so as to fill the space between the manual surgical instrument 200 and the housing 430.

(Advantageous Effects of Second Embodiment)

In a second embodiment, the following effects can be obtained.

In a second embodiment, as described above, the driven unit 420 of the interface 400 is configured such that one ends of the wires (421a, 422a, 423a, 424a) are wound around the shafts whereas the other ends of the wires (421a, 422a, 423a, 424a) are to be wound up by the drivers 75 so that winding of the wires moves the manipulation portions (421f, 422f, 422g, 423f, 423g, 424f) to operate the switch portions (204, 205a, 205b, 206). As a result, the switch portions of the manual surgical instrument 200 can be operated by the manipulation portions via the shafts by winding up the wires by the driving forces of the drivers 75 provided in the arm 60.

Further, in a second embodiment, as described above, the drivers 75 of the arm 60 are configured to perform the rotational drives, and the driven unit 420 includes the worms W and the worm wheels WW that decelerate the rotational drives (rotational speeds) from the drivers 75. As a result, the worms W and the worm wheels WW can increase the torques of the driving forces of the drivers 75 and transmit the increased torques to the manipulation portions (421f, 422f, 422g, 423f, 423g, 424f). Therefore, even in a case where relatively large operating forces are required to operate (press) the switch portions (204, 205a, 205b, 206) of the manual surgical instrument 200, the switch portions can be operated by the increased torques.

Further, in a second embodiment, as described above, the driven unit 420 includes the parallel link mechanism (422e, 423e) such that the parallel link mechanism is operated by the driving force transmitted from the driver 75 to move the plural manipulation portions (422f, 422g, 423f, 423g). As a result, the plural manipulation portions can be moved (driven) with the driving force from the one driver 75 by means of the parallel link mechanism, so that the configuration of the interface 400 can be simplified.

(Modifications)

Note that one or more embodiments disclosed herein should be considered as exemplary in all respects and do not limit the invention. The scope of the invention is indicated by claims, not by explanation of one or more embodiments described above, and includes equivalents to the claims and all alterations (modification) within the same.

For example, in first and second embodiments described above, the case has been described in which the switch portions of the manual surgical instrument 200 are operated by the manipulation portions of the interface. However, the disclosure is not limited thereto. For example, operation-target portions other than the switch portions, such as an operating lever, of the manual surgical instrument may be operated by the manipulation portions of the interface.

In first and second embodiments described above, the plural switch portions are provided to the manual surgical instrument 200. However, the disclosure is not limited thereto. For example, the manual surgical instrument may be provided with only one switch portion.

In a second embodiment described above, the case has been described in which the driven unit 420 includes both the wires and the shafts. However, the disclosure is not limited thereto. For example, the driven unit may be composed of wires only. The driven unit may be composed of a belt(s) or the like.

In first and second embodiments described above, the case has been described in which the manual surgical instrument 200 is the stapler. However, the disclosure is not limited thereto. The disclosure can also be applied to manual surgical instruments other than the stapler.

In an embodiment described above, the case has been described in which the number of the arms 60 provided is four. However, the disclosure is not limited thereto. The number of the arms 60 may be three or less.

In an embodiment described above, the case has been described in which each of the arm section 61 and the positioner 40 is configured as the 7-axis articulated robot. However, the disclosure is not limited thereto. For example, each of the arm 60 and the positioner 40 may be configured as an articulated robot other than the 7-axis articulated robot (for example, a 6-axis articulated robot, an 8-axis articulated robot, or the like).

The invention claimed is:

1. An interface for connecting a manual surgical instrument to a driver provided to a robotic arm in such a manner that the manual surgical instrument is operable by a driving force transmitted from the driver, wherein the manual surgical instrument includes a grip portion to be gripped by an operator and a switch portion provided at the grip portion and comprising a plurality of switches configured to be pressed by the operator, the interface comprising:
   a driven unit configured to be connected to the driver and be driven by the driving force transmitted from the driver;
   a manipulation portion comprising a plurality of manipulation portions configured to be driven by the driven unit and to manipulate the plurality of switches provided at the grip portion of the manual surgical instrument; and
   a surgical instrument holder configured to hold the manual surgical instrument at a position where the plurality of switches of the manual surgical instrument is positioned in correspondence with respect to positions of the plurality of manipulation portions.

2. The interface according to claim 1, wherein
   the manipulation portion of the interface is configured to be driven by the driving force transmitted through the driven unit to press the switch portion of the manual surgical instrument.

3. The interface according to claim 2, wherein
   the driven unit comprises a plurality of driven parts, and the plurality of manipulation portions correspond to the plurality of driven parts.

4. The interface according to claim 3, wherein
each of the driven parts comprises at least one of a wire and a shaft, and
the driving force of each of a plurality of drivers provided to the robotic arm is transmitted to a corresponding one of the plurality of manipulation portions via the at least one of the wire and the shaft.

5. The interface according to claim 2, wherein
the driven unit comprises at least one of a wire and a shaft, and
the driving force of the driver is transmitted to the manipulation portion via the at least one of the wire and the shaft.

6. The interface according to claim 1, wherein
the driven unit comprises a plurality of driven parts, and
the plurality of manipulation portions correspond to the plurality of driven parts.

7. The interface according to claim 6, wherein
each of the driven parts comprises at least one of a wire and a shaft, and
the driving force of each of a plurality of drivers provided to the robotic arm is transmitted to a corresponding one of the plurality of manipulation portions via the at least one of the wire and the shaft.

8. The interface according to claim 1, wherein
the driven unit comprises at least one of a wire and a shaft, and
the driving force of the driver is transmitted to the manipulation portion via the at least one of the wire and the shaft.

9. The interface according to claim 8, wherein
the driven unit includes the shaft and does not include the wire, and
the driven unit is configured to transmit the driving force from the driver to the manipulation portion via the shaft.

10. The interface according to claim 1, wherein
the surgical instrument holder is configured to accommodate therein the driven unit and the manipulation portion.

11. The interface according to claim 1, wherein
the surgical instrument holder includes a lock member configured to fix the manual surgical instrument being positioned with respect to the manipulation portion.

12. The interface according to claim 1, wherein
the surgical instrument holder includes a housing configured to hold the manual surgical instrument at the position where the switch portion of the manual surgical instrument is positioned with respect to the manipulation portion, and
a spacer is provided between the manual surgical instrument and the housing to fill a space between the manual surgical instrument and the housing.

13. An interface for connecting a manual surgical instrument to a driver provided to a robotic arm in such a manner that the manual surgical instrument is operable by a driving force transmitted from the driver, the interface comprising:
a driven unit configured to be connected to the driver and be driven by the driving force transmitted from the driver;
a manipulation portion configured to be driven by the driven unit and manipulate an operation-target portion of the manual surgical instrument; and
a surgical instrument holder configured to hold the manual surgical instrument at a position where the operation-target portion of the manual surgical instrument is positioned with respect to the manipulation portion, wherein
the driven unit comprises a wire and a shaft,
one side of the wire is wound around the shaft, and
the other side of the wire is driven to be wound up by the driver, in such a manner that winding of the wire by the driver moves the manipulation portion so as to operate the operation-target portion of the manual surgical instrument.

14. The interface according to claim 13, wherein
the driver of the robotic arm is configured to perform rotational drive, and
the driven unit further includes a speed reduction unit configured to decelerate a speed of the rotational drive transmitted from the driver.

15. The interface according to claim 14, wherein
the speed reduction unit includes a worm and a worm wheel.

16. The interface according to claim 13, wherein
the wire is connected to the shaft via a pulley.

17. An interface for connecting a manual surgical instrument to a driver provided to a robotic arm in such a manner that the manual surgical instrument is operable by a driving force transmitted from the driver, the interface comprising:
a driven unit configured to be connected to the driver and be driven by the driving force transmitted from the driver;
a manipulation portion configured to be driven by the driven unit and manipulate an operation-target portion of the manual surgical instrument; and
a surgical instrument holder configured to hold the manual surgical instrument at a position where the operation-target portion of the manual surgical instrument is positioned with respect to the manipulation portion, wherein
the manipulation portion includes a plurality of manipulation portions,
the driven unit includes a parallel link mechanism, and
the parallel link mechanism is configured to be driven by the driving force transmitted from the driver to move two or more of the plurality of manipulation portions.

18. An interface for connecting a manual surgical stapler to a driver provided to a robotic arm in such a manner that the manual surgical stapler is operable by a driving force transmitted from the driver, wherein the manual surgical stapler includes a grip portion to be gripped by an operator and a switch portion provided at the grip portion and comprising a plurality of switches configured to be pressed by the operator, the interface comprising:
a driven unit configured to be connected to the driver and be driven by the driving force transmitted from the driver;
a manipulation portion comprising a plurality of manipulation portions configured to be driven by the driven unit and to manipulate the plurality of switches provided at the grip portion of the manual surgical stapler; and
a surgical instrument holder configured to hold the manual surgical stapler at a position where the plurality of switches of the manual surgical stapler is positioned in correspondence with respect to positions of the plurality of manipulation portions.

19. A surgery assist robot comprising:
a robotic arm including a driver for driving a robotic surgical instrument; and an interface provided between the driver of the robotic arm and a manual surgical instrument, wherein the manual surgical instrument includes a grip portion to be gripped by an operator and a switch portion provided at the grip portion and comprising a plurality of switches configured to be pressed by the operator, wherein the interface includes:
a driven unit configured to be connected to the driver provided to the robotic arm and be driven by a driving force transmitted from the driver;
a manipulation portion comprising a plurality of manipulation portions configured to be driven by the driven unit and to manipulate the plurality of switches provided at the grip portion of the manual surgical instrument; and
a surgical instrument holder configured to hold the manual surgical instrument at a position where the plurality of switches of the manual surgical instrument is positioned in correspondence with respect to positions of the plurality of manipulation portions.

20. The surgery assist robot according to claim 19, wherein
the interface is attached to the robotic arm via a drape adaptor that holds a drape covering the robotic arm.

* * * * *